(12) United States Patent
Navratil et al.

(10) Patent No.: US 12,285,596 B2
(45) Date of Patent: Apr. 29, 2025

(54) IMPLANT APPLICATORS

(71) Applicant: ENVISIA THERAPEUTICS, INC., Morrisville, NC (US)

(72) Inventors: Tomas Navratil, Morrisville, NC (US); Akshay Nitish Nadkarni, Morrisville, NC (US); Gretchen Willard, Morrisville, NC (US); Andrew Corson, Morrisville, NC (US); Matthew Walker, Morrisville, NC (US)

(73) Assignee: Alcon Inc., Fribourg (CH)

( * ) Notice: Subject to any disclaimer, the term of this patent is extended or adjusted under 35 U.S.C. 154(b) by 1064 days.

(21) Appl. No.: 16/330,025

(22) PCT Filed: Sep. 5, 2017

(86) PCT No.: PCT/US2017/050122
§ 371 (c)(1),
(2) Date: Mar. 1, 2019

(87) PCT Pub. No.: WO2018/045386
PCT Pub. Date: Mar. 8, 2018

(65) Prior Publication Data
US 2019/0374380 A1      Dec. 12, 2019

Related U.S. Application Data

(60) Provisional application No. 62/383,129, filed on Sep. 2, 2016.

(51) Int. Cl.
*A61M 5/32* (2006.01)
*A61B 5/15* (2006.01)
(Continued)

(52) U.S. Cl.
CPC ..... *A61M 5/3286* (2013.01); *A61B 5/150396* (2013.01); *A61F 2/16* (2013.01);
(Continued)

(58) Field of Classification Search
CPC ........ A61F 9/0017; A61F 2/16; A61F 2/1662; A61F 9/007; A61F 9/013; A61F 9/0008;
(Continued)

(56) References Cited

U.S. PATENT DOCUMENTS 3,405,713 A * 10/1968 Solowey ............. A61M 5/3202
604/263
4,251,310 A    2/1981 Goldhaber
(Continued)

FOREIGN PATENT DOCUMENTS

CN    102716531 A    10/2012
CN    204246599 U    4/2015
(Continued)

OTHER PUBLICATIONS

International Search Report and Written Opinion for International Application No. PCT/US2016/043675 dated Nov. 29, 2016.
(Continued)

*Primary Examiner* — Brigid K Byrd
(74) *Attorney, Agent, or Firm* — K&L Gates LLP; Louis C. Cullman; Benjamin D. Heuberger

(57) ABSTRACT

An intracameral injector needle having a substantially cylindrical body defining a longitudinal flow path therein, and having a proximal end, a distal end, an outer peripheral face and a bevel region. A first bevel of the bevel region has a first bevel angle with respect to the outer peripheral face. A second bevel of the bevel region extends from the first bevel to the proximal end. The second bevel includes a tip of the intracameral injector needle, and has a second bevel angle with respect to the outer peripheral face, where the second bevel angle is different from the first bevel angle, the first bevel and the second bevel defining a transition therebetween. The transition is at least one of: (1) longitudinally positioned between the tip of the intracameral injector
(Continued)

needle and a location of a maximum width of the bevel region; and (2) vertically disposed at a position below 50% of a maximum height of the bevel region.

21 Claims, 16 Drawing Sheets

(51) Int. Cl.
*A61F 2/16* (2006.01)
*A61F 9/00* (2006.01)
*A61M 5/158* (2006.01)

(52) U.S. Cl.
CPC .......... *A61F 2/1662* (2013.01); *A61F 2/1691* (2013.01); *A61F 9/0008* (2013.01); *A61F 9/0017* (2013.01); *A61M 5/3202* (2013.01); *A61M 5/158* (2013.01); *A61M 2210/0612* (2013.01)

(58) Field of Classification Search
CPC .............. A61M 5/3286; A61M 5/3202; A61M 2210/0612; A61B 5/150396; A61B 5/150389; A61B 17/3468
See application file for complete search history.

(56) References Cited

U.S. PATENT DOCUMENTS

| | | | | |
|---|---|---|---|---|
| 5,224,950 | A * | 7/1993 | Prywes | A61F 9/0133 606/166 |
| 5,575,780 | A * | 11/1996 | Saito | A61M 5/3286 604/272 |
| 5,752,942 | A * | 5/1998 | Doyle | B24B 19/16 604/274 |
| 5,869,079 | A | 2/1999 | Wong et al. | |
| 6,129,710 | A | 10/2000 | Padgett et al. | |
| 7,753,916 | B2 | 7/2010 | Weber et al. | |
| 10,624,904 | B2 | 4/2020 | Williams et al. | |
| 10,849,656 | B2 | 12/2020 | Navratil et al. | |
| 11,116,776 | B2 | 9/2021 | Williams et al. | |
| 2001/0039402 | A1* | 11/2001 | Prais | B24B 19/16 604/274 |
| 2004/0151754 | A1 | 8/2004 | Ashton | |
| 2004/0171598 | A1 | 9/2004 | Bingaman et al. | |
| 2005/0154399 | A1* | 7/2005 | Weber | A61F 9/0017 606/107 |
| 2005/0244467 | A1 | 11/2005 | Nivaggioli et al. | |
| 2005/0244468 | A1 | 11/2005 | Huang et al. | |
| 2006/0233860 | A1 | 10/2006 | Chang et al. | |
| 2007/0031472 | A1 | 2/2007 | Huang et al. | |
| 2007/0224278 | A1 | 9/2007 | Lyons et al. | |
| 2008/0033351 | A1 | 2/2008 | Trogden et al. | |
| 2008/0071246 | A1 | 3/2008 | Nazzaro et al. | |
| 2009/0041924 | A1* | 2/2009 | Steube | A61M 5/329 204/192.15 |
| 2010/0124565 | A1 | 5/2010 | Spada et al. | |
| 2010/0278897 | A1 | 11/2010 | Shi et al. | |
| 2011/0229551 | A1 | 9/2011 | Doshi et al. | |
| 2013/0138047 | A1 | 5/2013 | Takemoto et al. | |
| 2013/0158561 | A1 | 6/2013 | Bhagat et al. | |
| 2013/0218102 | A1* | 8/2013 | Iwase | A61M 5/00 451/28 |
| 2013/0253528 | A1 | 9/2013 | Haffner et al. | |
| 2015/0118279 | A1 | 4/2015 | Ghebremeskel et al. | |
| 2015/0140062 | A1 | 5/2015 | Shiah et al. | |
| 2015/0209180 | A1 | 7/2015 | Prausnitz et al. | |
| 2015/0238687 | A1* | 8/2015 | Novakovic | A61M 5/158 604/502 |
| 2016/0067426 | A1 | 3/2016 | Ujaoney | |
| 2016/0206832 | A1* | 7/2016 | Kurose | A61F 9/007 |
| 2017/0252520 | A1* | 9/2017 | Higaki | A61B 17/3417 |
| 2017/0368268 | A1* | 12/2017 | Chopra | A61M 5/3286 |
| 2018/0368886 | A1 | 12/2018 | Navratil et al. | |
| 2019/0083512 | A1 | 3/2019 | Williams et al. | |

FOREIGN PATENT DOCUMENTS

| | | |
|---|---|---|
| WO | 2014/036009 A1 | 3/2014 |
| WO | 2015/085251 A1 | 6/2015 |
| WO | 2015/126694 A1 | 8/2015 |
| WO | 2016/144832 A1 | 9/2016 |
| WO | 2017/015604 A1 | 1/2017 |
| WO | 2018/045386 A1 | 3/2018 |

OTHER PUBLICATIONS

Singaporean Search Report and Written Opinion for Singaporean Application No. 11201800538R (date of actual completion of search: Nov. 2, 2018).
Supplementary European Search Report for European Patent Application No. 16762267.9 dated Oct. 15, 2018 (8 pages).
International Search Report and Written Opinion for International Application No. PCT/US2016/021081 dated Jul. 18, 2016.
International Search Report and Written Opinion for International Application No. PCT/US2017/050122 dated Nov. 16, 2017.
Singaporean Written Opinion (Second) for Singaporean Application No. 11201800538R (date of written opinion: Oct. 11, 2019).
U.S. Appl. No. 16/712,624, filed Dec. 12, 2019.
Extended European Search Report, dated Dec. 8, 2020, for European Patent Application Serial No. 20191361.3.
Singaporean Written Opinion, dated Apr. 20, 2020, for Singaporean Patent Application Serial No. 11201901588T.
Singaporean Written Opinion, dated Mar. 5, 2021, for Singaporean Patent Application Serial No. 11201901588T.
Singaporean Written Opinion, dated Nov. 13, 2020, for Singaporean Patent Application Serial No. 11201800538R.
U.S. Appl. No. 17/066,363, filed Oct. 8, 2020, abandoned.
Lambiase et al., An update on intravitreal implants in use for eye disorders. Drugs of Today, 50(3):239-249 (2014).

* cited by examiner

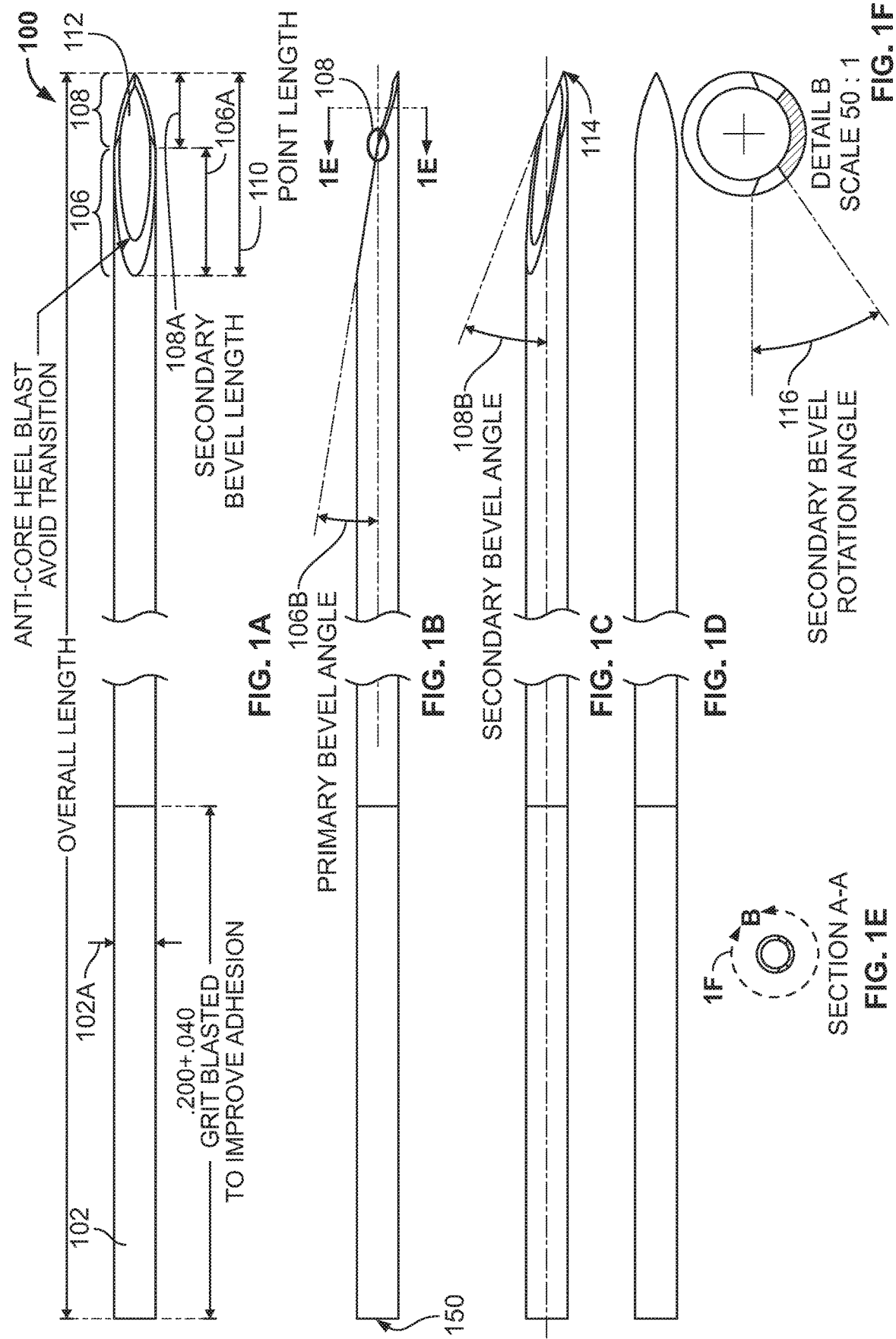

| SPECIFICATIONS ISO 7864: 1993(E) | |
|---|---|
| OVERALL LENGTH | 0.748" ± .010" |
| PRIMARY BEVEL ANGLE (PRIMARY GRIND ANGLE) | 9.5 ± 2 DEGREES |
| POINT LENGTH (BEVEL LENGTH) | 0.079" ± .010" |
| SECONDARY BEVEL LENGTH (LANCET LENGTH) | 0.025" ± .010" |
| SECONDARY BEVEL ANGLE (SECONDARY GRIND ANGLE) | 20 ± 2 DEGREES |
| SECONDARY BEVEL ROTATION ANGLE | 30 ± 2 DEGREES |
| HYPODERMIC MEDICAL GRADE 304 SS | 275 XTW<br>OD 0.0160" - 0.0165"<br>ID 0.0115" - 0.0130"<br>NOM WT 0.0020" |

FIG. 1G

| SPECIFICATIONS ISO 7864: 1993(E) | |
|---|---|
| OVERALL LENGTH | 0.467" ± .010" |
| PRIMARY BEVEL ANGLE (PRIMARY GRIND ANGLE) | 6 ± 2 DEGREES |
| POINT LENGTH (BEVEL LENGTH) | 0.133" ± .010" |
| SECONDARY BEVEL LENGTH (LANCET LENGTH) | 0.045" ± .010" |
| SECONDARY BEVEL ANGLE (SECONDARY GRIND ANGLE) | 13 ± 2 DEGREES |
| SECONDARY BEVEL ROTATION ANGLE | 35 ± 2 DEGREES |
| HYPODERMIC MEDICAL GRADE 304 SS | 275 XTW<br>OD 0.0160" - 0.0165"<br>ID 0.0115" - 0.0130"<br>NOM WT 0.0020" |

FIG. 2G

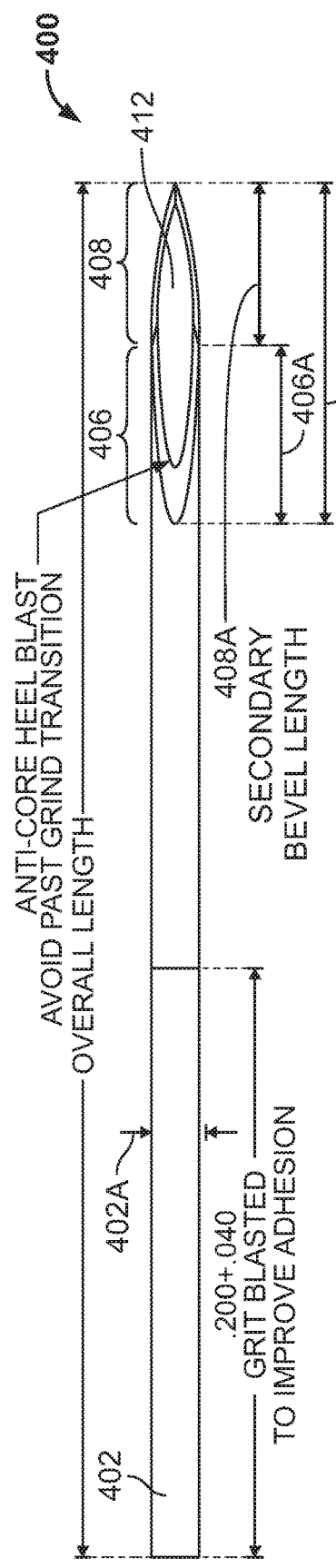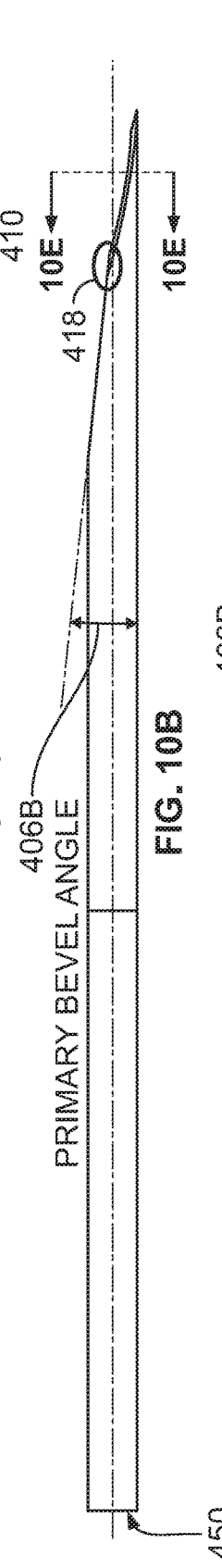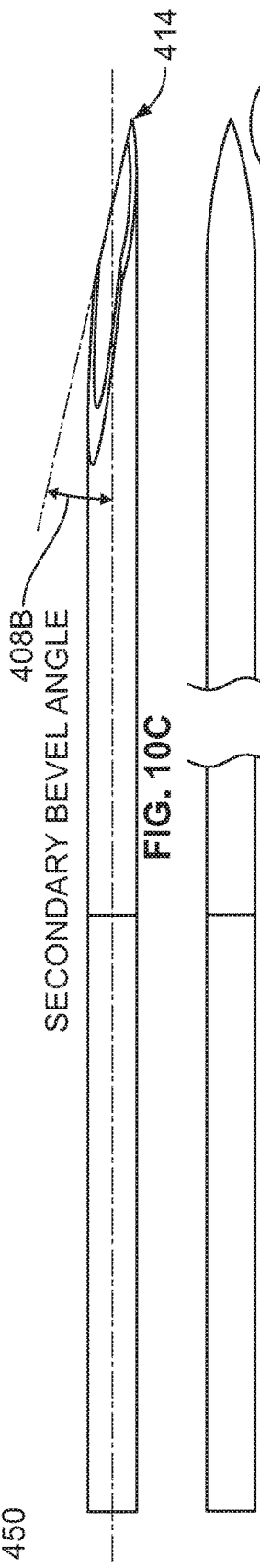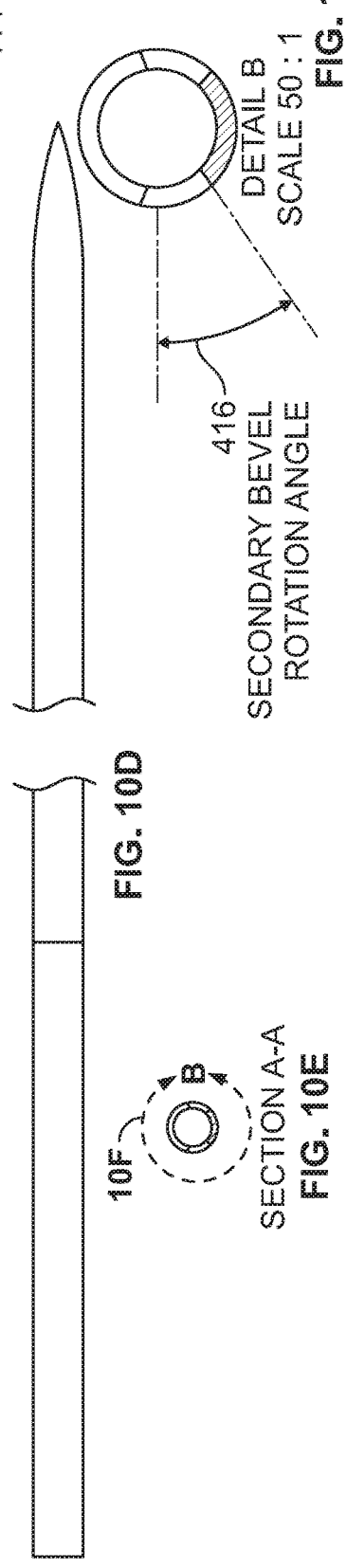
FIG. 10A
FIG. 10B
FIG. 10C
FIG. 10D
FIG. 10E
FIG. 10F

| SPECIFICATIONS ISO 7864: 1993(E) | |
|---|---|
| OVERALL LENGTH | 0.467" ± .010" |
| PRIMARY BEVEL ANGLE (PRIMARY GRIND ANGLE) | 6 ± 2 DEGREES |
| POINT LENGTH (BEVEL LENGTH) | 0.118" ± .010" |
| SECONDARY BEVEL LENGTH (LANCET LENGTH) | 0.055" ± .010" |
| SECONDARY BEVEL ANGLE (SECONDARY GRIND ANGLE) | 13 ± 2 DEGREES |
| SECONDARY BEVEL ROTATION ANGLE | 35 ± 2 DEGREES |
| HYPODERMIC MEDICAL GRADE 304 SS | 275 XTW<br>OD 0.0160" - 0.0165"<br>ID 0.0115" - 0.0130"<br>NOM WT 0.0020" |

IMPLANT APPLICATORS

This application is a 35 U.S.C. § 371 National Stage Entry of PCT/US2017/050122, filed Sep. 5, 2017, which claims the benefit of U.S. Provisional Application No. 62/383,129, filed Sep. 2, 2016, and titled "Implant Applicators," the entire contents of which are herein expressly incorporated by reference.

This application for letters patent disclosure document describes inventive aspects that include various novel innovations (hereinafter "disclosure") and contains material that is subject to copyright, mask work, and/or other intellectual property protection. The respective owners of such intellectual property have no objection to the facsimile reproduction of the disclosure by anyone as it appears in published Patent Office file/records, but otherwise reserve all rights.

FIELD

Embodiments of the current disclosure are directed toward needle designs and associated implant delivery devices, for example for delivering drugs to an eye of a patient.

BACKGROUND

The use of intraocular injections has been gaining prevalence worldwide, and was the most commonly performed ophthalmic procedure in the United States in 2015. Currently, a majority of intraocular injections are administered intravitreally for the treatment of age-related macular degeneration (AMD) and diabetic macular edema (DME) with anti-vascular endothelial growth factor (anti-VEGF) agents such as intravitreal bevacizumab, ranibizumab, and aflibercept.

SUMMARY

Embodiments described herein relate generally to medical implant delivery apparatuses and methods.

In some embodiments, an intracameral injector needle has a substantially cylindrical body defining a longitudinal flow path therein. The body has a proximal end, a distal end, an outer peripheral face and a bevel region, with the longitudinal flow path extending from the proximal end to the distal end. A first bevel of the bevel region has a first bevel angle with respect to the outer peripheral face. A second bevel of the bevel region extends from the first bevel to the proximal end. The second bevel includes a tip of the intracameral injector needle, and has a second bevel angle with respect to the outer peripheral face, where the second bevel angle is different from the first bevel angle, the first bevel and the second bevel defining a transition therebetween. The bevel region has a tapered width. The transition is at least one of: (1) longitudinally positioned between the tip of the intracameral injector needle and a location of a maximum width of the bevel region; and (2) vertically disposed at a position below 50% of a maximum height of the bevel region.

The first bevel angle with respect to the outer peripheral face can be between about 7.5 degrees and about 11.5 degrees, for example about 9.5 degrees.

The second bevel angle with respect to the outer peripheral face can be between about 18 degrees and about 22 degrees, for example about 20 degrees.

The transition can be positioned at a distance that is greater than or less than a corneal thickness for the tip of the needle. For example, the transition can be positioned at one of less than 500 µm and greater than 600 µm from the tip of the intracameral injector needle.

In some embodiments, an intraocular injection device comprises an intracameral injector needle with a substantially cylindrical body defining a longitudinal flow path therein. The body has a proximal end, a distal end, an outer peripheral face and a bevel region, with the longitudinal flow path extending from the proximal end to the distal end. A first bevel of the bevel region has a first bevel angle with respect to the outer peripheral face. A second bevel of the bevel region extends from the first bevel to the proximal end. The second bevel includes a tip of the intracameral injector needle, and has a second bevel angle with respect to the outer peripheral face, where the second bevel angle is different from the first bevel angle, the first bevel and the second bevel defining a transition therebetween. The bevel region has a tapered width. The transition is at least one of: (1) longitudinally positioned between the tip of the intracameral injector needle and a location of a maximum width of the bevel region; and (2) vertically disposed at a position below 50% of a maximum height of the bevel region. The first bevel angle with respect to the outer peripheral face can be between about 7.5 degrees and about 11.5 degrees, for example about 9.5 degrees. The second bevel angle with respect to the outer peripheral face can be between about 18 degrees and about 22 degrees, for example about 20 degrees. The transition can be positioned at a distance that is greater than or less than a corneal thickness for the tip of the needle. For example, the transition can be positioned at one of less than 500 µm and greater than 600 µm from the tip of the intracameral injector needle.

In some embodiments, an intraocular injection device further comprises: a cap having a proximal end, a distal end, and a longitudinal axis, the cap including a bristle retainer at least partially disposed therewithin at the distal end thereof, the bristle retainer having a bristle at least partially disposed therewithin; a needle hub at least partially disposed within the cap; the intracameral injector needle disposed within a hub pocket of the needle hub; an applicator connected to the needle hub; and at least one implant disposed within the intracameral injector needle, the intracameral injector needle and the at least one implant substantially aligned with one another along the longitudinal axis of the cap.

In some embodiments, a method of administering an implant to a patient comprises: providing an intraocular injection device, including a preloaded needle hub assembly and an applicator handle, the preloaded needle hub assembly including: the intracameral injector needle of claim 1 or claim 7, an implant, and a bristle disposed within a bristle retainer; applying force to the intracameral injector needle to penetrate a biological membrane; and actuating the applicator handle such that the implant is linearly advanced through the intracameral injector needle.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 1A-1G are schematic drawings of a first intracameral injector needle design (Design A), according to some embodiments.

FIGS. 2A-2G are schematic drawings of a second intracameral injector needle design (Design B), according to some embodiments.

FIGS. 10A-10G are schematic drawings of a comparative needle design (Design D).

DETAILED DESCRIPTION OF SOME OF THE EMBODIMENTS

Multiple novel ophthalmologic therapies have been designed to be administered via intracameral injection into the anterior chamber of the eye via clear peripheral corneal injection for the treatment of glaucoma with intraocular pressure (TOP) lowering agents. Examples of such therapies include extended release intracameral bimatoprost or ENV515 extended release intracameral travoprost (ENV515), currently in clinical development.

Additionally, novel intracocular needle designs specifically optimized for injections via clear peripheral cornea are needed for anterior chamber paracentesis to, for example, relieve elevated intraocular pressure during acute angle closure glaucoma, to create side ports during cataract surgery, and/or for other applications when a transcorneal injection needs to be performed or transcorneal channel needs to created.

The position of entry and ease of penetration of the injecting needle are important factors in determining the degree of damage to ocular tissue caused by the injection-based therapy. For example, scarring in certain portions of the eye can lead to a degradation in visual acuity.

Embodiments of the present disclosure relate to improved needle designs and associated implant delivery devices for delivering drugs to an eye of a patient. Such designs and devices can promote improved tolerability of trans-corneal drug implantation in patients.

Novel Needle Designs with Exceptional Sharpness

ENV515 was designed to be administered via intracameral injection through clear, peripheral cornea with the injection site being approximately 1,000 um within the limbus (the transition between the cornea and the conjunctiva). To support effective intracameral administration of ENV515 and all other intraocular therapies via other intraocular injections including but not limited to intravitreal injections, the inventors have surprisingly discovered that needle Designs A (shown and described, by way of example, with reference to FIGS. 1, 4, 6 and 8) and B (shown and described, by way of example, with reference to FIGS. 2, 5, 7 and 9) (also referred to herein as "intracameral injector needles") have exceptional sharpness and thus are particularly useful for intracameral, transcorneal injections and delivery of ENV515 and other intraocular therapies.

Figure 3:
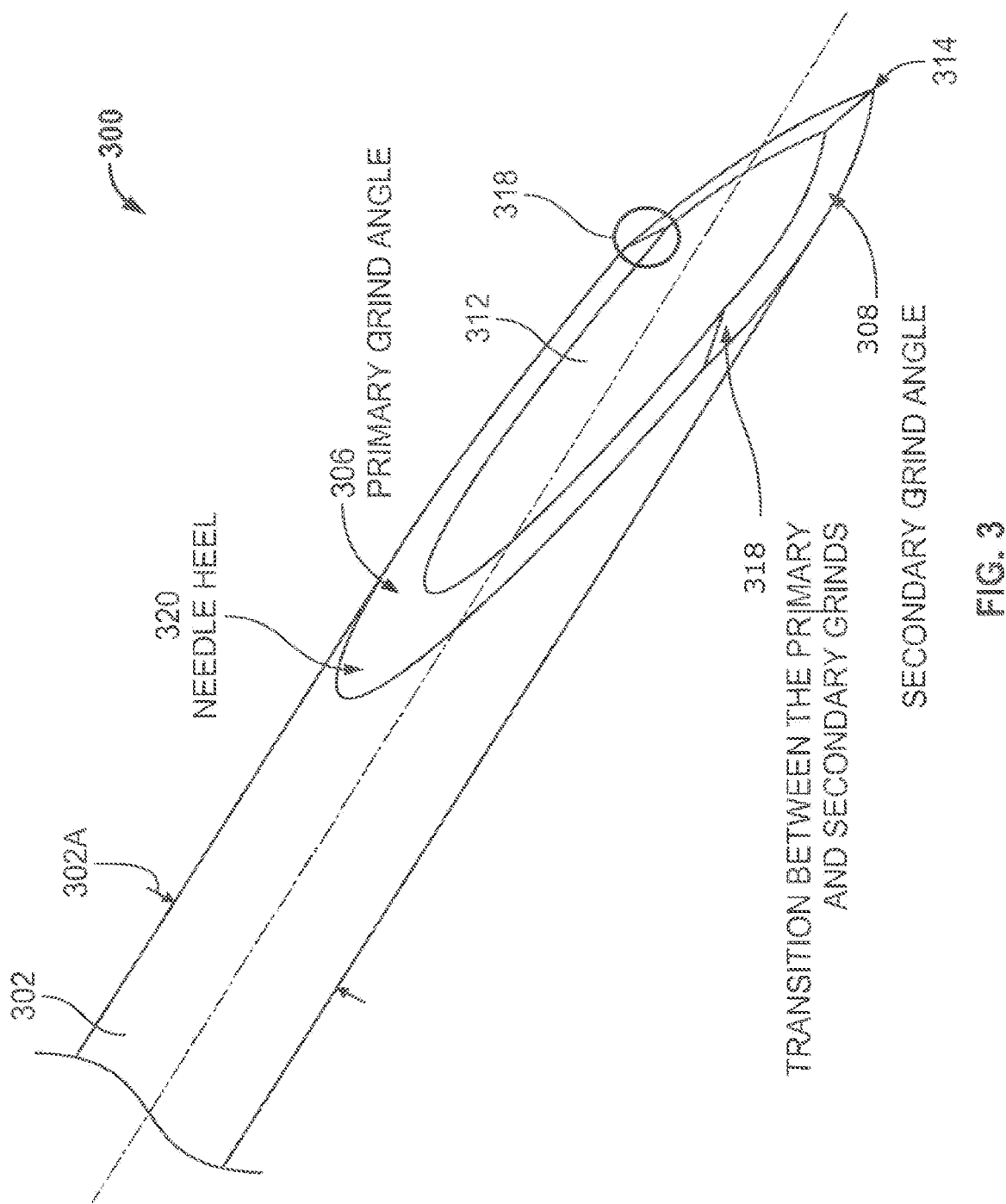
FIG. 3 is a schematic illustration of a transition between a primary grind angle and a secondary grind angle.

Without wishing to be bound by theory, the unexpected sharpness of the needles manufactured according to Designs A and B is believed to be at least in part attributed to novel structural features of the needle Designs A and B wherein the transition between a primary grind and a secondary grind of the needle bevel occurs before the needle bevel width reaches the outer diameter of the needle tube (here, directionality is described with the start at the needle tip and moving longitudinally along the needle from the tip to the transition between the grinds, and subsequently to the needle heel—see the overview discussion of FIG. 3, below). In other words, in exemplary needle Designs A and B, the transition between the primary grind and the secondary grind is positioned between the needle tip and the position along the longitudinal axis of the needle at which the needle bevel reaches its maximum width. The maximum bevel width can be equal or substantially equal to the outer diameter of the needle tubing.

In some embodiments, the transition is positioned at a distance from the tip of the intracameral injector needle that is different from the thickness of the human cornea, so as to control when (i.e., at what stage during the injection process) the transition moves through the cornea. For example, the transition can be positioned less than 500 μm (e.g., 450 μm) or greater than 600 μm (e.g., 650 μm) from the tip of the intracameral injector needle. An example transition is identified by circling 318 in FIG. 3. Example dimensions and positioning of the transition within the bevel of the needle are provided in FIGS. 4 and 5 for Designs A and B, respectively, and it is also present as a structural feature in all Figures and schematics related to Designs A and B. Additional side and top views of the Designs A and B are displayed in FIGS. 6-9, as discussed in greater detail below.

A secondary design feature arises as a result of this transition occurring before the needle bevel width reaches the outer diameter of the needle tube, which also contributes to needle sharpness. In Designs A and B, this transition point occurs at a height below 50% of the full height of the needle, relative to the bottom of the needle (which height may also be referred to as the diameter of the needle body or shaft, excluding the bevel region). This positioning of the transition point relative to the height of the needle is shown and explicitly dimensioned in FIG. 4 for Design A and FIG. 5 for Design B.

Needle Architecture Terminology

FIG. 3 presents an overview of structural features of injector needles, according to some embodiments. As shown in FIG. 3, the needle 300 includes a body or "shaft" portion 302 with a width 302A (orthogonal to the longitudinal dimension of the needle, also referred to herein as a "height" or "diameter"), and having a tip (or "proximal") end 314. A "bevel" region comprises the portion of the needle that extends from the needle heel 320 to the tip 314. The bevel region defines a lumen 312 (also referred to herein as an orifice or aperture), and includes a primary grind angle 306 that extends from the needle heel 320 to the transition 318. The bevel region also includes a secondary grind angle 308 that extends from the tip 314 to the transition 318. Note that there is a transition between the primary and secondary grinds on both sides (e.g., a left side and a right side) of the needle lumen 312.

Description of Design A

Turning now to FIGS. 1A-1G, a needle architecture 100 is shown. FIG. 1A shows a needle having a body or "shaft" portion 102 with a width 102A (orthogonal to the longitudinal dimension of the needle, also referred to herein as a "height" or "diameter"), and having a distal end 150 and a tip (or "proximal") end 114. FIG. 1A shows a top view of the needle, showing a lumen 112 at the proximal end, the lumen 112 defined within a bevel region comprising a primary bevel 106 (also referred to herein as a "primary grind") and a secondary bevel 108 (also referred to herein as a "secondary grind"). The primary bevel has a length 106A and the secondary bevel has a length 108A. The primary bevel length 106A and the secondary bevel length 108A, collectively, define a "point length" 110. FIG. 1B is a first side view of the Design A needle, showing the primary bevel angle 106B (also referred to herein as a "primary grind angle") and the transition point 118 between the primary bevel and the secondary bevel. FIG. 1C is a second, perspective side view of the Design A needle, showing the secondary bevel angle 108B (also referred to herein as a "secondary grind angle") and the tip 114 of the needle. FIG. 1D is a reverse/back view of the needle. FIG. 1E shows an end view of the needle, as viewed along section A-A of FIG. 1B. FIG. 1F is a zoomed view of the reverse/back view of the needle, showing a secondary bevel rotation angle 116 with respect to a midline of the needle cross-section. The secondary bevel rotation angle 116 is a dependent variable, an example of which is shown in FIG. 1G. The secondary bevel rotation angle 116 is applied in two different planes from which the primary bevel is applied (e.g., the primary bevel rotation angle) in a clockwise and a counterclockwise rotation of the needle along the longitudinal axis by a specified amount (e.g., 30±2 degrees) relative to the primary bevel rotation angle. The manufacturing specifications shown in FIG. 1G were used to manufacture the Design A needles for clinical use.

Although not explicitly recited in the chart of FIG. 1G, the first length of the first bevel can be readily obtained based on the difference between the point length of the bevel region and the second length of the second bevel (e.g., point length–second length). The length of the second bevel (e.g., the second length) is shown as 0.025 inches±0.010 inches (e.g., 0.015 to 0.035 inches), while the point length of the bevel region, which includes the first bevel and the second bevel, is shown as 0.079 inches±0.010 inches (e.g., 0.069 to 0.089 inches). This yields a range of potential length of the first bevel of 0.054±0.020 inches (e.g., upper bound=0.089−0.015=0.074 inches and lower bound=0.069−0.035=0.034 inches; or 0.054±0.020 inches). These individual ranges may also be expressed as a ratio of lengths, where the lower bound of the second bevel length divided by the upper bound of the first bevel length gives the ratio range's upper bound and the lower bound of the second bevel length divided by the upper bound of the first bevel length gives the ratio range's lower bound. In the case shown in FIG. 1G, this ratio will be recognized to yield a ratio between the nominal values for the respective lengths of 1:2.16 (e.g., 0.025:0.054) with ratios for the extremes of 1:4.93 and 1:0.97.

Figure 4:
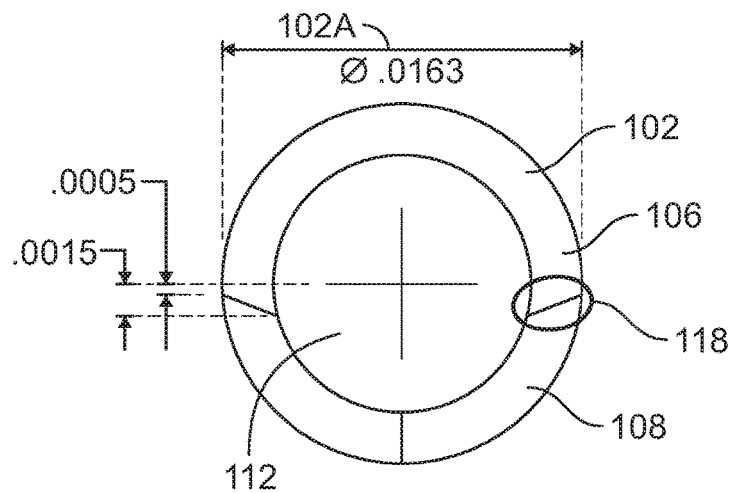
FIG. 4 is a schematic drawing of a front view of the needle design of FIGS. 1A-1E.
Figure 6:
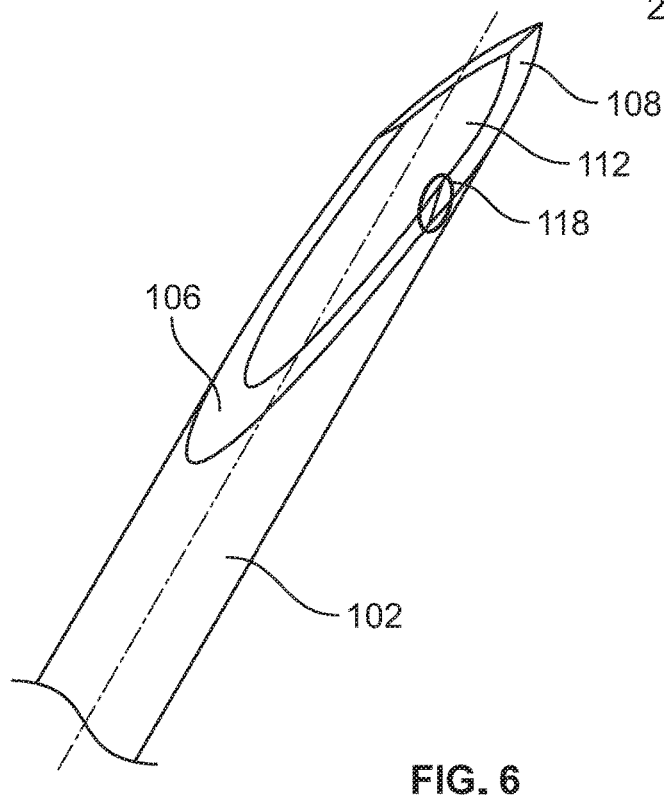
FIG. 6 is a schematic drawing of a side view of the needle design of FIGS. 1A-1E.
Figure 8:
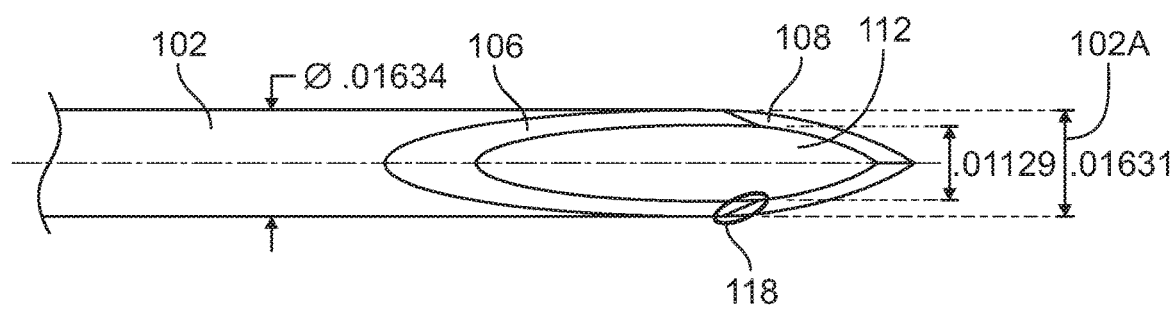
FIG. 8 is a schematic drawing of a top view of the needle design of FIGS. 1A-1E.

FIG. 4 shows an end view of the Design A needle with shaft 102, where the needle width (or height) 102A is about 0.0163 inches (0.0163"), and the transition 118 is positioned between 0.0005" and 0.0015" below the midline of the needle cross-section. Lumen 112 is centrally positioned, and the primary bevel 106 and secondary bevel 108 are also shown. FIG. 6 shows a perspective view of the Design A needle, also showing the transition 118, the lumen (or "orifice") 112, and the primary bevel 106 and secondary bevel 108. FIG. 8 is a top view of the Design A needle, also showing the transition 118, the lumen (or "orifice") 112, and the primary bevel 106 and secondary bevel 108. The diameter of the needle shaft outside the bevel region is shown in FIG. 8 to be about 0.01634", and the maximum width 102A of the bevel region is shown to be 0.01631," which by design is smaller than the maximum outer diameter of the needle. The lumen 112 has a maximum width of 0.01129".

Description of Design B

Figure 2A:
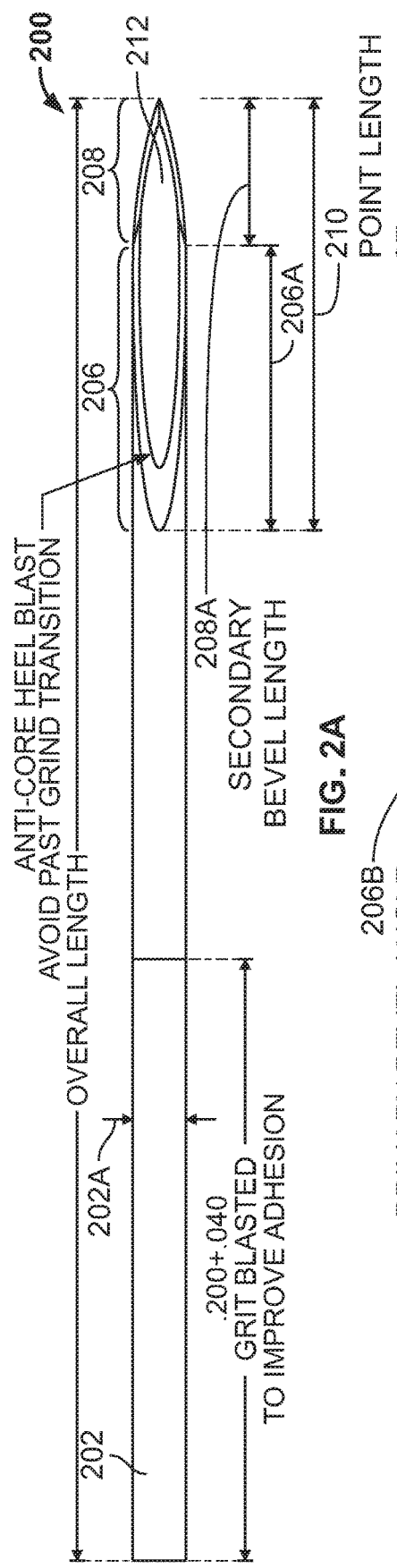
Figure 2B:
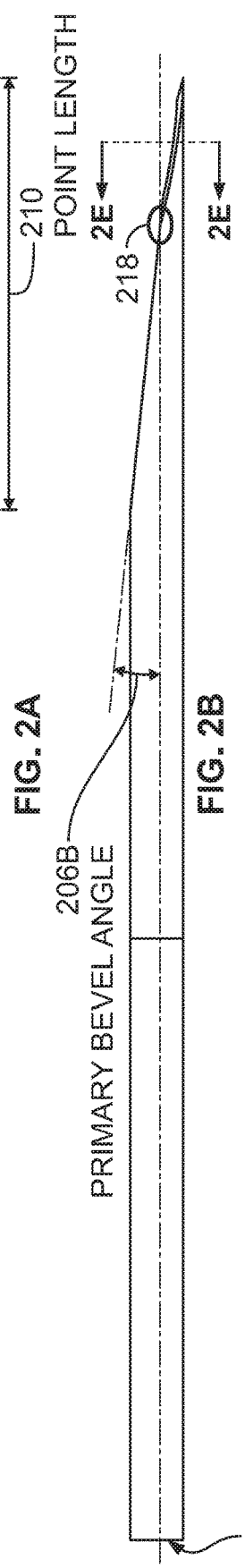
Figure 2C:
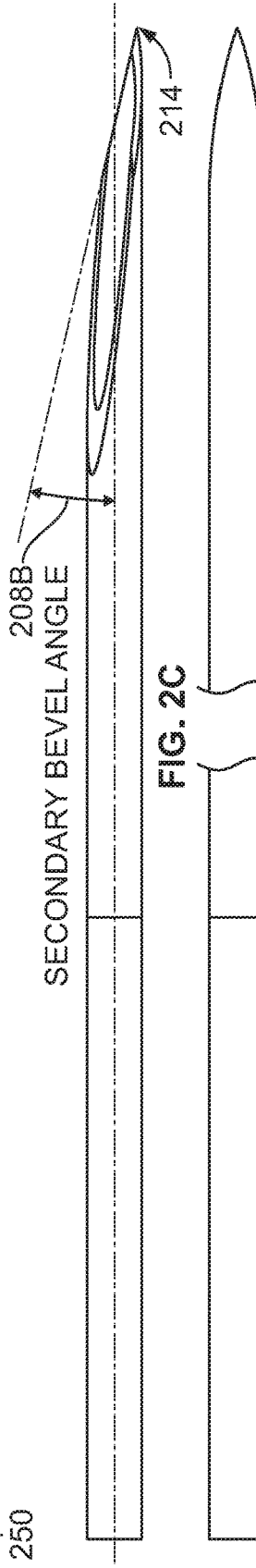
Figure 2D:
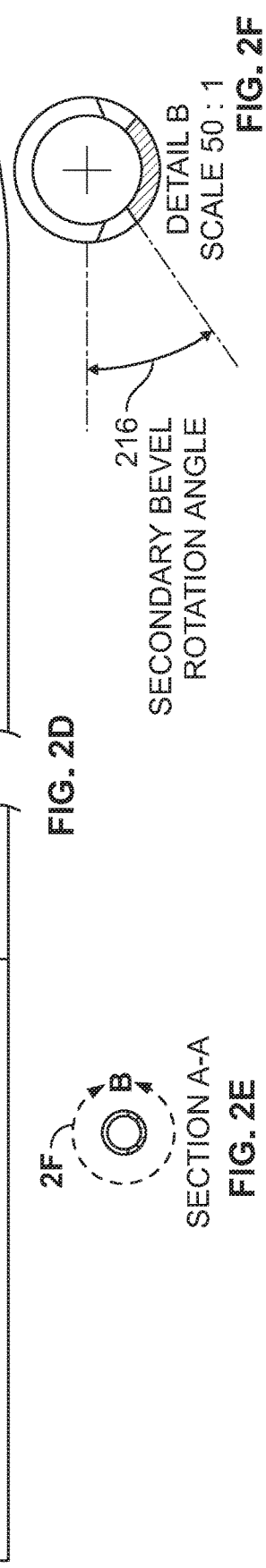
Figure 2E:
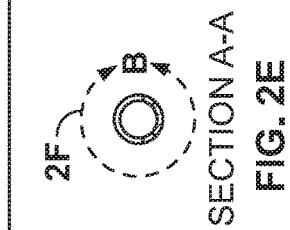
Figure 2F:
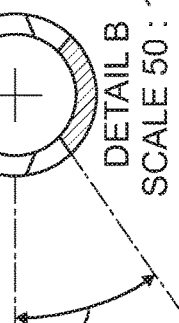

With reference to FIGS. 2A-2G, a needle architecture 200 is shown. FIG. 2A shows a needle having a body or "shaft" portion 202 with a width 202A (orthogonal to the longitudinal dimension of the needle, also referred to herein as a "height" or "diameter"), and having a distal end 250 and a tip (or "proximal") end 214. FIG. 2A shows a top view of the needle, showing a lumen 212 at the proximal end, the lumen 212 defined within a bevel region comprising a primary bevel 206 (also referred to herein as a "primary grind") and a secondary bevel 208 (also referred to herein as a "secondary grind"). The primary bevel has a length 206A and the secondary bevel has a length 208A. The primary bevel length 206A and the secondary bevel length 208A, collectively, define a "point length" 210 (which may also be referred to as an overall bevel length). FIG. 2B is a first side view of the Design B needle, showing the primary bevel angle 206B (also referred to herein as a "primary grind angle") and the transition point 218 between the primary bevel and the secondary bevel. FIG. 2C is a second, perspective side view of the Design B needle, showing the secondary bevel angle 208B (also referred to herein as a "secondary grind angle") and the tip 214 of the needle. FIG. 2D is a reverse/back view of the needle. FIG. 2E shows an end view of the needle, as viewed along section A-A of FIG. 2B. FIG. 2F is a zoomed view of the reverse/back view of the needle, showing a secondary bevel rotation angle 216 with respect to a midline of the needle cross-section. The secondary bevel rotation angle 216 is a dependent variable, an example of which is shown in FIG. 2G. The secondary bevel rotation angle 216 is applied in two different planes from which the primary bevel is applied (e.g., the primary bevel rotation angle) in a clockwise and a counterclockwise rotation of the needle along the longitudinal axis by a specified amount (e.g., 35±2 degrees) relative to the primary bevel rotation angle. The manufacturing specifications shown in FIG. 2G were used to manufacture the Design B needles for clinical use.

Although not explicitly recited in the chart of FIG. 2G, the first length of the first bevel can be readily obtained based on the difference between the point length of the bevel region and the second length of the second bevel (e.g., point length–second length). The length of the second bevel (e.g., the second length) is shown as 0.045 inches±0.010 inches (e.g., 0.035 to 0.055 inches), while the point length of the bevel region, which includes the first bevel and the second bevel, is shown as 0.133 inches±0.010 inches (e.g., 0.123 to 0.143 inches). This yields a range of potential length of the first bevel of 0.088±0.020 inches (e.g., upper bound=0.143−0.035=0.108 inches and lower bound=0.123−0.055=0.068 inches; or 0.088±0.020 inches). These individual ranges may also be expressed as a ratio of lengths, where the lower bound of the second bevel length divided by the upper bound of the first bevel length gives the ratio range's upper bound and the lower bound of the second bevel length divided by the upper bound of the first bevel length gives the ratio range's lower bound. In the case shown in FIG. 2G, this ratio will be recognized to yield a ratio between the nominal values for the respective lengths of 1:1.96 (e.g., 0.045:0.088) with ratios for the extremes of 1:3.09 and 1:1.24.

Figure 5:
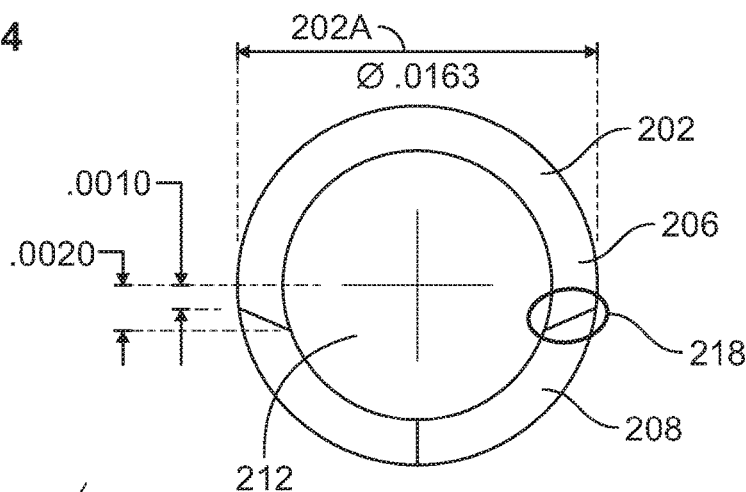
FIG. 5 is a schematic drawing of a front view of the needle design of FIGS. 2A-2E.
Figure 7:
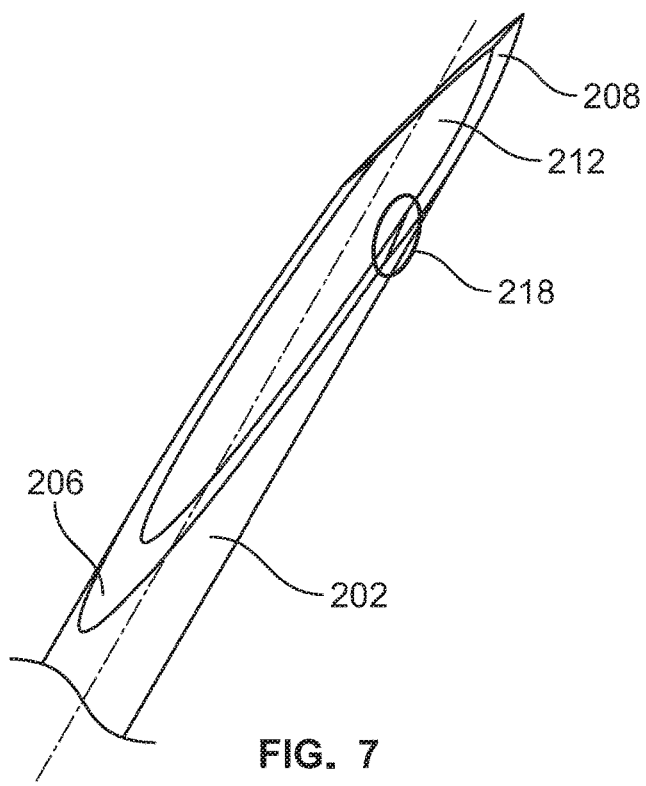
FIG. 7 is a schematic drawing of a side view of the needle design of FIG. 2A-2E.
Figure 9:
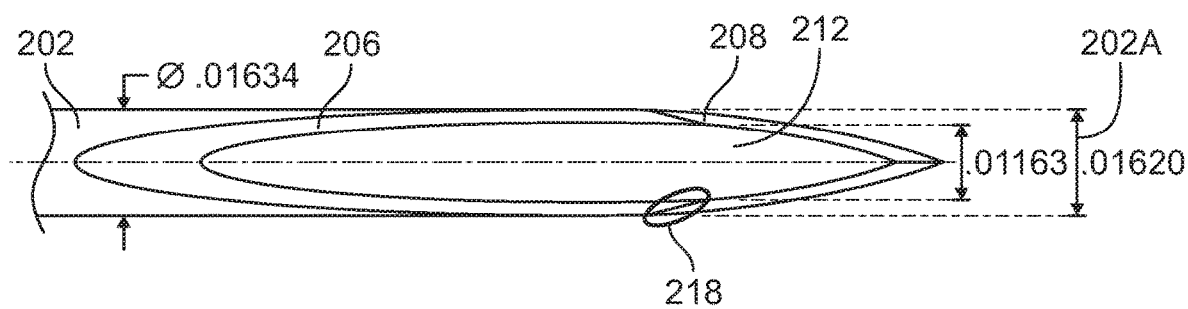
FIG. 9 is a schematic drawing of a top view of the needle design of FIG. 2A-2E.

FIG. 5 shows an end view of the Design B needle with shaft 202, where the needle width (or height) 202A is about 0.0163 inches (0.0163"), and the transition 218 is positioned between 0.0010" and 0.0020" below the midline of the needle cross-section. Lumen (or "orifice") 212 is centrally positioned, and the primary bevel 206 and secondary bevel 208 are also shown. FIG. 7 shows a perspective view of the Design B needle, also showing the transition 218, the lumen (or "aperture") 212, and the primary bevel 206 and secondary bevel 208. FIG. 9 is a top view of the Design B needle, also showing the transition 218, the lumen (or "orifice") 212, and the primary bevel 206 and secondary bevel 208. The diameter of the needle shaft outside the bevel region is shown in FIG. 9 to be about 0.01634", and the maximum width 102A of the bevel region is shown to be 0.01620," which by design is smaller than the maximum outer needle diameter. The lumen 212 has a maximum width of 0.01163".

Comparison with Existing Needle Designs

The performance of needle Designs A and B was compared with a reference "Design D," where the needle of Design D lacks the structural features described above (i.e., the transition between grind surfaces of the bevel is not positioned as described with reference to the embodiments set forth herein). Needle Design D is less sharp than needle Designs A and B, since the transition between the primary and secondary angle grinds occurs in the bevel after (or longitudinally beyond) the bevel has reached its maximum width, as measured while longitudinally traversing the needle from tip to heel, and after the needle bevel width reached the outer diameter of the needle tube. In needle Design D, such transition occurs between the heel of the needle (see reference numeral 320 in FIG. 3) and the point at which the bevel reaches its maximum width. For all structural dimensions of needle Design D, see FIGS. 10-13. As a result, the transition point in Design D occurs above 50% of the full height of the needle, relative to the bottom of the needle. This geometry is shown in FIGS. 11-12.

The Design D needle architecture 400 is shown in FIGS. 10A-10G. FIG. 10A shows a needle having a body or "shaft" portion 402 with a width 402A (orthogonal to the longitudinal dimension of the needle, also referred to herein as a "height" or "diameter"), and having a distal end 450 and a tip (or "proximal") end 414. FIG. 10A shows a top view of the needle, showing a lumen 412 at the proximal end, the lumen 412 defined within a bevel region comprising a primary bevel 406 (also referred to herein as a "primary grind") and a secondary bevel 408 (also referred to herein as a "secondary grind"). The primary bevel has a length 406A and the secondary bevel has a length 408A. The primary bevel length 406A and the secondary bevel length 408A, collectively, define a "point length" 410. FIG. 10B is a first side view of the Design D needle, showing the primary bevel angle 406B (also referred to herein as a "primary grind angle") and the transition point 418 between the primary bevel and the secondary bevel. FIG. 10C is a second, perspective side view of the Design D needle, showing the secondary bevel angle 408B (also referred to herein as a "secondary grind angle") and the tip 414 of the needle. FIG. 10D shows a reverse/back side view of the needle. FIG. 10E shows an end view of the needle, as viewed along section A-A of FIG. 10B. FIG. 10F is a zoomed view of the reverse/back view of the needle, showing a secondary bevel rotation angle 416 with respect to a midline of the needle cross-section. The secondary bevel rotation angle 416 is a dependent variable, an example of which is shown in FIG. 10G. The secondary bevel rotation angle 416 is applied in two different planes from which the primary bevel is applied (e.g., the primary bevel rotation angle) in a clockwise and a counterclockwise rotation of the needle along the longitudinal axis by a specified amount (e.g., 35±2 degrees) relative to the primary bevel rotation angle. The manufacturing specifications shown in FIG. 10G were used to manufacture the Design D needles.

Although not explicitly recited in the chart of FIG. 10G, the first length of the first bevel can be readily obtained based on the difference between the point length of the bevel region and the second length of the second bevel (e.g., point length–second length). The length of the second bevel (e.g., the second length) is shown as 0.055 inches±0.010 inches (e.g., 0.045 to 0.065 inches), while the point length of the bevel region, which includes the first bevel and the second bevel, is shown as 0.118 inches±0.010 inches (e.g., 0.108 to 0.128 inches). This yields a range of potential length of the first bevel of 0.063±0.020 inches (e.g., upper bound=0.128−0.045=0.083 inches and lower bound=0.108−0.065=0.043 inches; or 0.063±0.020 inches). These individual ranges may also be expressed as a ratio of lengths, where the lower bound of the second bevel length divided by the upper bound of the first bevel length gives the ratio range's upper bound and the lower bound of the second bevel length divided by the upper bound of the first bevel length gives the ratio range's lower bound. In the case shown in FIG. 10G, this ratio will be recognized to yield a ratio between the nominal values for the respective lengths of 1:1.15 (e.g., 0.055:0.063) with ratios for the extremes of 1:1.84 and 1:0.66.

Figure 11:
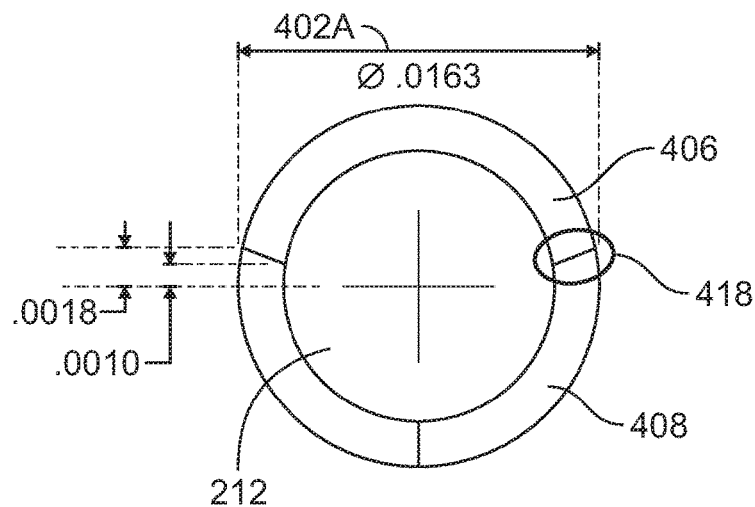
FIG. 11 is a schematic drawing of a front view of the needle design of FIGS. 10A-10E.
Figure 12:
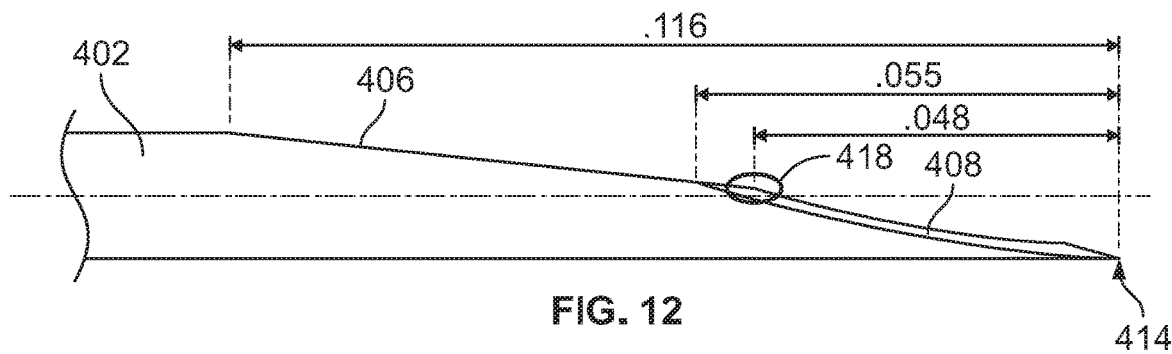
FIG. 12 is a schematic drawing of a side view of the needle design of FIGS. 10A-10E.
Figure 13:
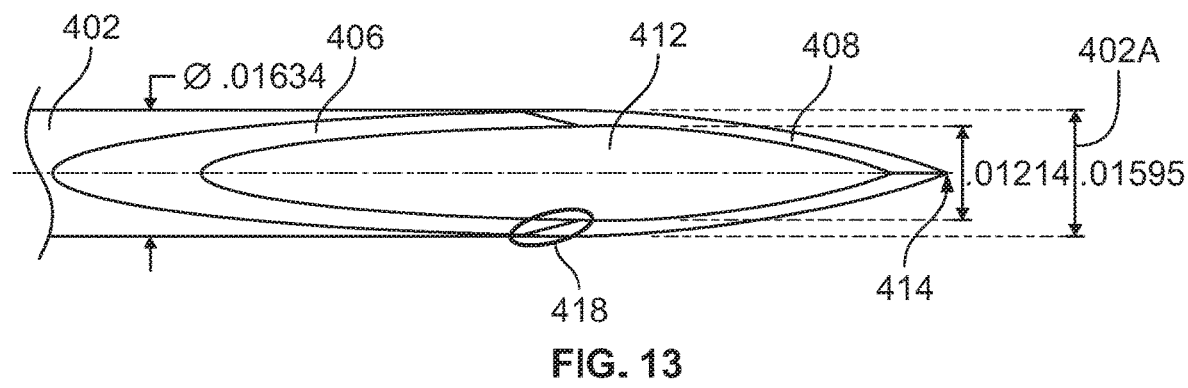
FIG. 13 is a schematic drawing of a top view of the needle design of FIGS. 10A-10E.

FIG. 11 shows an end view of the Design D needle, where the needle width (or height) 402A is about 0.0163", and the transition 418 is positioned between 0.0010" and 0.0018"

above the midline of the needle cross-section. Lumen (or "orifice") 412 is centrally positioned, and the primary bevel 406 and secondary bevel 408 are also shown. FIG. 12 is a side view of the Design D needle, showing the shaft 402, transition 418, the primary bevel 406 and secondary bevel 408, and the tip 414. FIG. 13 is a top view of the Design D needle, also showing the shaft 402, the transition 418, the lumen (or "orifice") 412, and the primary bevel 406 and secondary bevel 408. The diameter of the needle shaft outside the bevel region is shown in FIG. 13 to be about 0.01634", and the width 402A of the bevel region in the transition from the primary bevel to the secondary bevel is shown to be 0.01595". The lumen 412 has a maximum width of 0.01214".

Sharpness Assessments Via Force Measurements

Figure 14:
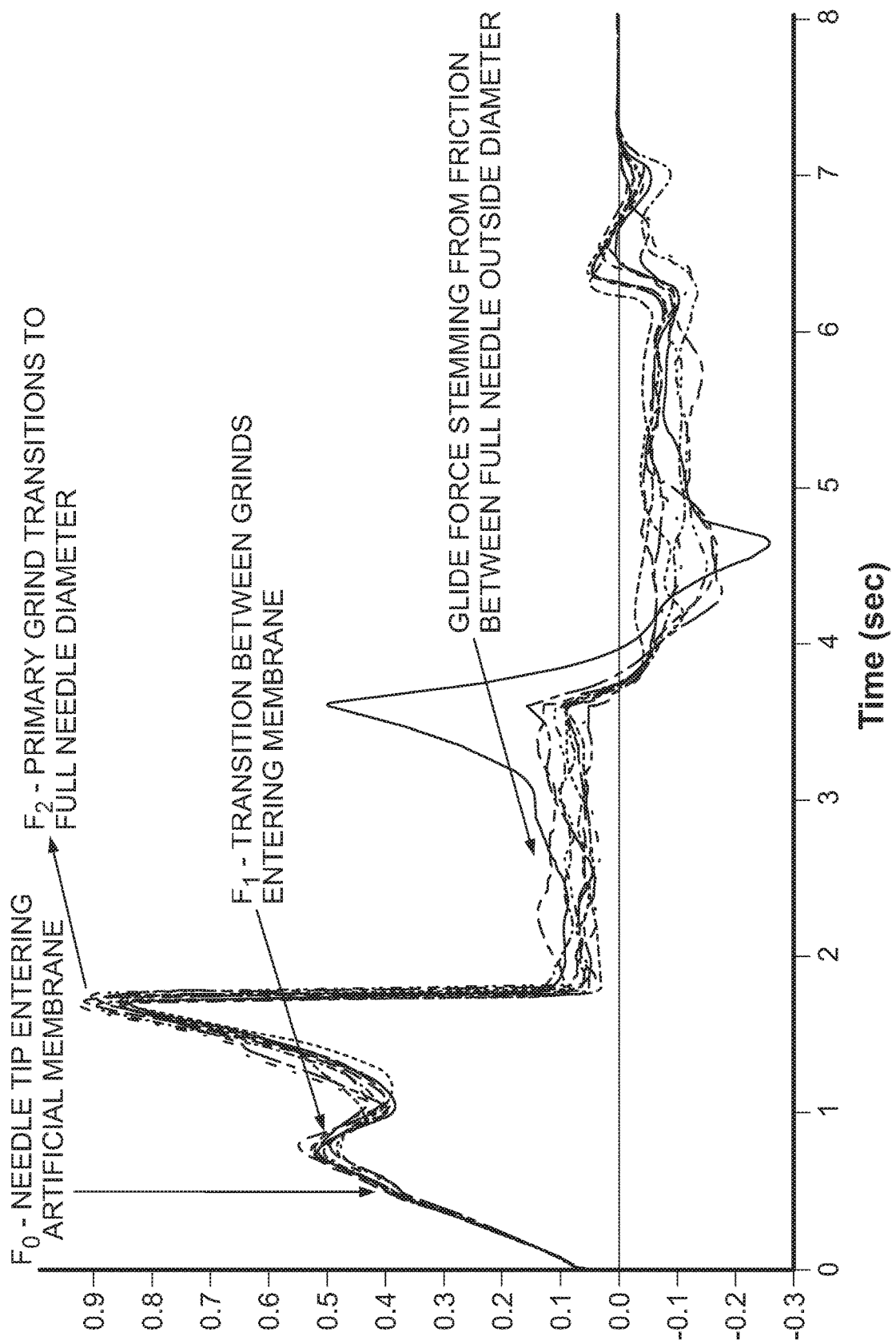
FIG. 14 is a plot of needle insertion force for the needle design of FIGS. 1A-1E.

Needle sharpness was assessed via needle insertion force measurements at a constant penetration speed (100 mm/min). Each needle was inserted into an artificial membrane mimicking a human cornea, and the force of insertion was measured. Force curves for needle Design A are shown in FIG. 14. There are several transient force peaks that correlate to different structural features of the needle during insertion into the membrane:
  F0—Needle tip entering artificial membrane
  F1—Transition between primary and secondary grinds entering membrane
  F2—Primary grind transitions to full needle diameter
  Glide force stemming from friction between full needle outside diameter For comparison, a U.S. FDA 510K approved and commercially distributed needle was used as a control—a 27 gauge (ga) regular wall needle distributed by Becton Dickinson (BD). Needle Designs A, B and D were manufactured as 27 ga needles per the specifications set forth in FIGS. 1-9 by established commercial needle manufacturers and tested for needle insertion force. Full force curves are shown in FIG. 14 for needle Design A, and table of key forces (including F0, F1, F2 and glide force, as defined above) are provided for needle Designs A, B, D and for the control 27 ga regular wall BD needle in Table 1.

TABLE 1

Insertion Force Measurements (all measurements in Newtons (N))

|  | F0 | F1 | F2 | Glide |
|---|---|---|---|---|
| Design A |  |  |  |  |
| Mean | 0.4033 | 0.4641 | 0.8353 | 0.0623 |
| STD | 0.0494 | 0.0487 | 0.0506 | 0.0163 |
| Design B |  |  |  |  |
| Mean | 0.36024 | 0.473637 | 0.794877 | 0.12606 |
| STD | 0.050926 | 0.040583 | 0.079865 | 0.20377 |
| Design D |  |  |  |  |
| Mean | 0.3761 | 0.7184 | 0.5541 | 0.1106 |
| STD | 0.0481 | 0.0354 | 0.0941 | 0.0135 |
| BD Control |  |  |  |  |
| Mean | 0.4041 | 0.4966 | 0.6582 | 0.0283 |
| STD | 0.1070 | 0.0510 | 0.0375 | 0.0044 |

As will be appreciated from the values recited in Table 1, the range of the measured force values for F0 with respect to design A are 0.4033±0.0494 Newtons (N) and the range of the measured force values for F1 are 0.4641±0.0487 N. When the lower range of F0 is compared to the upper range of F1 a ratio of 1:0.917605478 is obtained (e.g., 0.4527:0.4154), which may be truncated to 1:0.91. When the upper range of F0 is compared to the upper range of F1 a ratio of 1:1.448996892 is obtained (e.g., 0.3539:0.5128), which may be truncated to 1:1.44.

As will be appreciated from the values recited in Table 1, the range of the measured force values for F0 with respect to design B are 0.36024±0.050926 Newtons (N) and the range of the measured force values for F1 are 0.473637±0.040583 N. When the lower range of F0 is compared to the upper range of F1 a ratio of 1:1.053233974 is obtained (e.g., 0.411166:0.433054), which may be truncated to 1:1.05. When the upper range of F0 is compared to the upper range of F1 a ratio of 1:1.662453041 is obtained (e.g., 0.309314:0.51422), which may be truncated to 1:1.66.

As will be appreciated from the values recited in Table 1, the range of the measured force values for F0 with respect to design D are 0.473637±0.0481 Newtons (N) and the range of the measured force values for F1 are 0.7184±0.0354 N. When the lower range of F0 is compared to the upper range of F1 a ratio of 1:1.61008958 is obtained (e.g., 0.4242:0.683), which may be truncated to 1:1.61. When the upper range of F0 is compared to the upper range of F1 a ratio of 1:2.298170732 is obtained (e.g., 0.328:0.7538), which may be truncated to 1:2.30.

Relevance of the Measured Forces and of the F1 Force

It has been previously determined that the F1 insertion force is particularly important for penetration of human peripheral cornea during intracameral injections in human patients during ENV515 administration. Previously, human patients were injected intracamerally with a needle for which F1 was measured to be ~1.2 N. Such needles were not capable of penetrating a human cornea well during intracameral injection, and could result in tissue damage to the cornea. A separate group of human patients was injected intracamerally with a needle for which F1 was measured to be ~0.69 N. Such needles performed well. Based on these observations in human patients, needles with an F1 penetration force of less than 0.69 N would perform well in human patients during intracameral injections and during intracameral administration of ENV515, and needles with smaller F1 force would perform better than needles with larger F1 forces. Based on the F1 forces of ~0.46 N and ~0.47 N for needle Designs A and B (see Table 1, above), these needles are superior for intracameral injection applications and for ENV515 administration, when compared with the control BD needle. Needle Designs A and B are particularly preferred for intracameral injections, other intraocular injections, and any injections in general.

Intracameral Injections in Rabbit Eyes

Enucleated rabbit eyes and needles manufactured according to Designs A, B, D and the control BD needles were used by a medical doctor with ophthalmology specialty training, and skilled research and development (R&D) personnel, both trained in intracameral injections, to inject the enucleated rabbit eyes via intracameral injection. Needle Designs A and B were found to be superior for intracameral injections compared to needle Design D and the control BD needle based on the ease of insertion (or penetration force) during the intracameral injections.

Experimental Results—Intracameral Implant Insertion ENV515 (travoprost) Intracameral Implants were inserted into the anterior chamber of an eye using an insertion tool referred to as the ENV515 Gen 3 Implant Applicator which succeeds the ENV515 Phase 2b-3A Implant Applicator. The applicator is a platform for delivery of the ENV515 (travoprost) Intracameral Implant. Example implant applicators are shown and described in related International Patent Application No. PCT/US2016/021081, the entire contents of which are herein expressly incorporated by reference.

The applicator is supplied as a single-use, sterile, 27 gauge needle-based instrument for delivery of the ENV515 implants into the anterior chamber. The applicator includes two separate parts and is supplied in two separate sterile packages: one containing the ENV515 Gen 3 Implant Applicator needle hub assembly (part number 10539-325-211 RevF ENV515 Generation 3 Implant Applicator—Needle Hub Assembly) and one containing the ENV515 Phase 2b-3A Implant Applicator handle (part number 10539-325-149 Handle Assembly). The ENV515 Phase 2b-3A Implant Applicator handle was designed and tested to be usable with multiple needle hub assemblies including both ENV515 Phase 2b-3A Implant Applicator needle hub assembly and the ENV515 Gen 3 Implant Applicator needle hub assembly. The ENV515 Gen 3 Implant Applicator uses a custom manufactured (according to Design A, as shown and described with reference to FIGS. 1A-1G), 27 gauge, single-lumen hypodermic needle manufactured by established hypodermic needle manufacturer ISPG, Inc. to deliver the ENV515-3-2 (travoprost) Intracameral Implant. The manufacturing specifications shown in FIG. 1G were used to manufacture the Design A needles for clinical use. The ENV515 Phase Gen 3 Implant Applicator needle hub assembly and handle are terminally sterilized via gamma irradiation following assembly and packaging.

For the ENV515-01 Phase 2a clinical study, Cohort 3 (ENV515-01 Phase 2a study protocol incorporating Amendment 05), the ENV515 Gen 3 Implant Applicator including the ENV515 Gen 3 Implant Applicator needle hub assembly and the ENV515 Phase 2b-3A Implant Applicator handle, and the ENV515-3-2 (travoprost) Intracameral Implants are packaged separately, and the implants will be loaded into the applicator in a sterile field prior to administration to patients with glaucoma.

It is contemplated that an applicator can be used in a manner such that sterile ENV515 implants are preloaded into the sterile implant applicator, with the needle hub assembly of the implant applicator functioning as a container closure for the implants.

Implant Applicator Design, Manufacture and Use

As discussed above, the ENV515 Gen 3 Implant Applicator is designed utilizing a custom manufactured, 27 gauge, single-lumen hypodermic needle manufactured by established hypodermic needle manufacturer ISPG, Inc. and molded, machined or off-the-shelf components manufactured from medical grade materials. A stainless steel metal shaft actuated via scroll wheel advances the rod-shaped ENV515 implants from the lumen of the needle.

A complete design history file has been established and maintained per 21 CFR 820, covering: design and development planning, design input, design output, design review, pilot design verification, design transfer, and history of design changes, and including: reports for User Needs and Requirements, Applicator User Feedback, Hazard Analysis, Design Failure Modes and Effects Analysis (DFMEA), and Certificate of Conformance for the Design. The design of the ENV515 Phase 2b-3A Implant Applicator handle (part number 10539-325-149 Handle Assembly) is described herein with reference to FIG. 16. The design history file includes inspections for all purchased or manufactured components in compliance with the Component Quality Plan and Component Certificate of Conformance and inspections for device assembly in compliance with the EG-Gilero manufacturer's Component and Subassembly Quality Control Plan and Assembly Certificate of Conformance.

The ENV515 Phase Gen 3 Implant Applicator is designed and manufactured as a scroll-wheel actuated dry applicator that utilizes a stainless steel shaft to eject ENV515 (travoprost) Intracameral Implants from the lumen of the applicator needle. The ENV515 Phase Gen 3 Implant Applicator is supplied in two separate sterile packages: one containing the ENV515 Gen 3 Implant Applicator needle hub assembly (part number 10539-325-211 RevF ENV515 Generation 3 Implant Applicator—Needle Hub Assembly) and one containing the ENV515 Phase 2b-3A Implant Applicator handle (part number 10539-325-149 Handle Assembly). The ENV515 Phase 2b-3A Implant Applicator handle was designed and tested to be usable with multiple needle hub assemblies including both ENV515 Phase 2b-3A Implant Applicator needle hub assembly and the ENV515 Gen 3 Implant Applicator needle hub assembly.

The ENV515 Gen 3 Implant Applicator is manufactured for use in the ENV515-01 Phase 2a Cohort 3 clinical study submitted under the current IND (ENV515-01 Phase 2a Study Protocol incorporating Amendment 05). In the ENV515-01 Phase 2a Cohort 3 clinical study, the ENV515-3-2 (travoprost) Intracameral Implants will be loaded into the ENV515 Gen 3 Implant Applicator immediately prior to use by the trained personnel in the ENV515-01 Phase 2a Cohort 3 clinical study, following mandatory training on the loading and injection procedures.

The design of the ENV515 Phase Gen 3 Implant Applicator consists of the ENV515 Gen 3 Implant Applicator needle hub assembly (part number 10539-325-211 RevF ENV515 Generation 3 Implant Applicator—Needle Hub Assembly) and the ENV515 Phase 2b-3A Implant Applicator handle (part number 10539-325-149 Handle Assembly. The design for the ENV515 Gen 3 Implant Applicator needle hub assembly is included in FIG. 15. The materials used in the ENV515 Gen 3 Implant Applicator needle hub assembly are provided in Table 2 below. The design for the ENV515 Phase 2b-3A Implant Applicator handle is included in FIG. 16. The materials used in the ENV515 Phase 2b-3A Implant Applicator handle are provided in Table 2.

Figure 15:
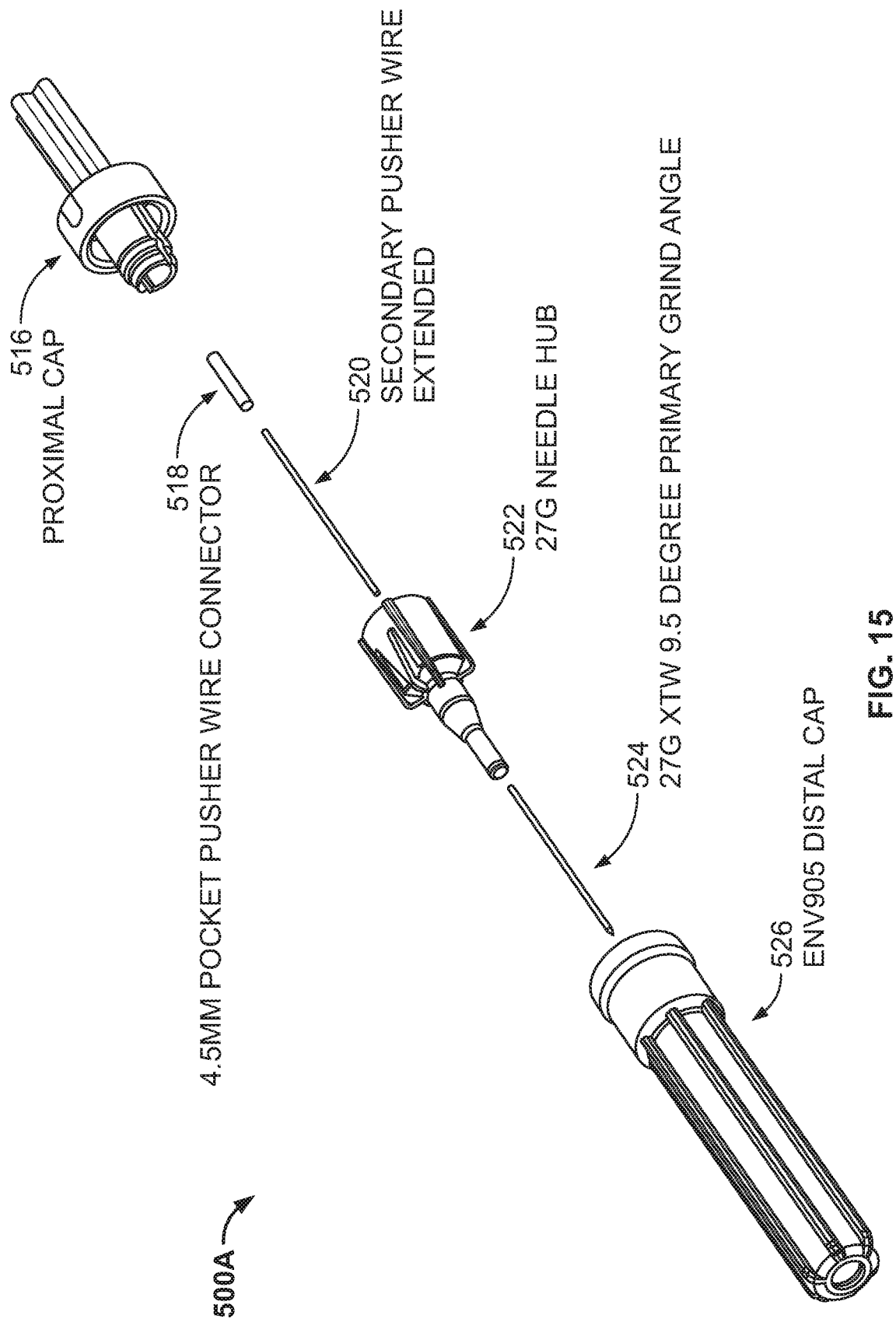
FIG. 15 is an exploded view of an applicator needle hub assembly, according to some embodiments.

FIG. 15 is an exploded view of an applicator needle hub assembly, showing internal components thereof, according to some embodiments. As shown in FIG. 15, an applicator needle hub assembly 500A includes a proximal cap 516, a distal cap 526, a pocket pusher wire connector 518, an extended secondary pusher wire 520, a needle hub 522, and a needle 524 (e.g., the intracameral injector needle of FIGS. 1A-1E or FIGS. 2A-2E).

TABLE 2

Materials Used in the ENV515 Gen 3 Implant Applicator Needle Hub Assembly (10539-325-211 RevF ENV515 Generation 3 Implant Applicator - Needle Hub Assembly)

| Part Number | Qty | Component | Material | Comments |
|---|---|---|---|---|
| 10539-325-209 REVA 27G NEEDLE HUB | 1 | Custom, injection molded | MAKROLON RX1805 COLOR: CLEAR TINT | Injection molding grade of transparent polycarbonate formulated to provide increased resistance to chemical attack from IV (intravenous) fluid products, such as lipid emulsions. Makrolon RX1805 is designated as "medical-grade" and has met the requirements of the FDA-Modified ISO 10993, Part 1 "Biological Evaluation of Medical Devices" tests with human tissue contact time of 30 days or less. |
| 10539-325-232 REVD 27G XTW 9.5 DEGREE PRIMARY GRIND ANGLE NEEDLE | 1 | Custom, drawn stainless steel ground for sharpness | 304SS | Custom ground needle from medical grade hypo tube. |
| 10539-325-107 RevD 4.5 MM Pocket Pusher Wire Connector | 1 | Custom, machined | TECANAT UNFILLED POLYCARBONATE COLOR: WHITE | Machine grade natural unfilled polycarbonate that has transparency, excellent impact strength and tensile properties |
| 10539-325-233 REVA SECONDARY PUSHER WIRE EXTENDED | 1 | Custom | MATERIAL: 304 STAINLESS STEEL | Spring Temper per ASTMA313 |
| 10539-325-161 REVB ENV905 DISTAL CAP | 1 | Custom, injection molded | P5M6K-080 POLYPROPYLENE WITH POLYONE 9103-FT-50 ANTI-STAT ADDITIVE COLOR: CLEAR | Clarified, Gamma Radiation Sterilizable Random Copolymer with anti-static additive |
| 10539-325-105 REVE PROXIMAL CAP | 1 | Custom, injection molded | PP PRO-FAX PF511 COLOR: CLEAR | Radiation resistant, high melt flow, controlled rheology polypropylene homo-polymer is available in pellet form. This resin is typically used in injection molding applications and offers retention of physical properties and color after radiation sterilization and good processability. This resin resists yellowing and embrittlement after gamma radiation. |
| REF UV ADHESIVE LOCTITE 3942 | 1 | OTS purchased component | MATERIAL: LOCTITE 3942 | Medium viscosity, UV/Visible light curing acrylic adhesive suitable for applications that require fast cure, flexibility, high adhesion and autoclave resistance. It is ISO 10993 Biological Tested for use in the assembly of disposable medical devices |
| 10539-325-126 REVA POUCH1 NHA | 1 | OTS purchased component | MATERIAL: HEAT SEAL COATED DUPONT TYVEK & 48 GA PET/1.5 MIL PE (35791-E) | Standard medical device packaging material manufactured of a layer of 1073B Tyvek Uncoated bonded to PET 48 Gauge film. Not included in biocomp tests but in contact with components prior to test |
| REF UV ADHESIVE LOCTITE 3926 | 1 | OTS purchased component | MATERIAL: LOCTITE 3926 | High viscosity, UV/Visible light curing acrylic adhesive suitable for applications that require fast cure, flexibility, high adhesion and autoclave resistance. It is ISO 10993 Biological Tested of use in the assembly of disposable medical devices |
| 10539-270-02 REVA NEEDLE LUBRICATION FORMULATION | 1 | Custom chemical combination | MDX4-4159 combined with Heptane and IPA solvents | Medical grade dispersion consisting of the following constituents (v/v): 6% MDX4-4159 65.8% Heptane solvent 28.2% IPA solvent Solvents flash off following coating of cannula. Stainless steel, coated with a cured layer of Dow Corning MDX4- 4159, 50% Medical Grade Dispersion, has been fully evaluated to meet the requirements of "Biomedical Grade" materials produced by Dow Corning |

Figure 16:
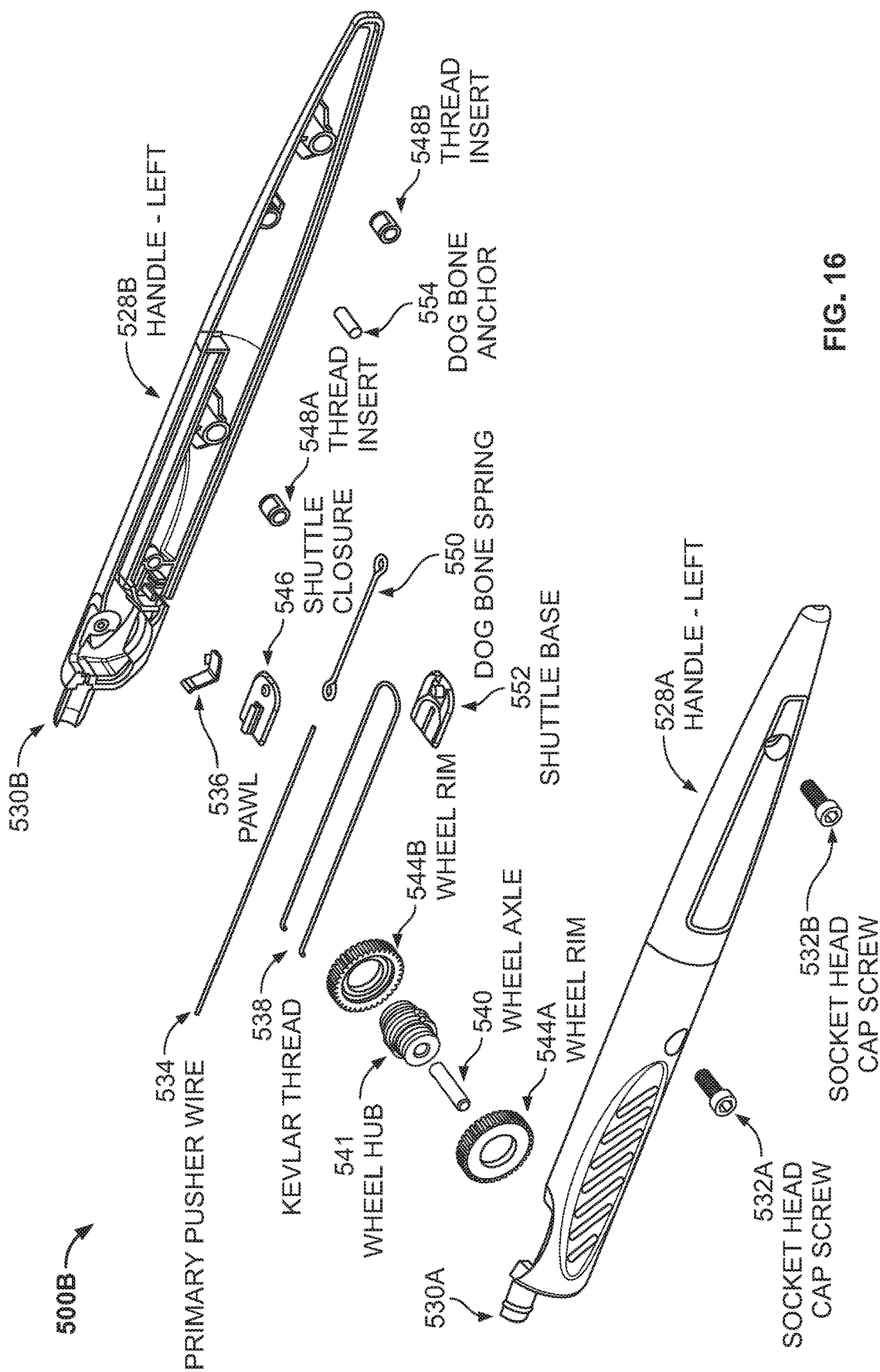
FIG. 16 is an exploded view of an applicator handle, compatible with the applicator needle hub assembly of FIG. 15, according to some embodiments.

FIG. 16 is an exploded view of an applicator handle, compatible with the applicator needle hub assembly of FIG. 15, according to some embodiments. As shown in FIG. 16, an applicator handle 500B includes a left handle 528A and a right handle 530A, configured to be coupled and secured to one another, for example via socket head cap screws 532A and 532B and thread inserts 548A and 548B. Once left handle 528A and right handle 530A are coupled together, a connector region is formed by portions 530A and 530B, and this connector region can be configured to mate with an applicator needle hub assembly. The applicator handle 500B also includes wheel rims 544A and 544B, wheel axle 540, and wheel hub 541 (collectively, a "wheel subassembly"), Kevlar thread 538, primary pusher wire 534, shuttle base 552, dog bone spring 550, dog bone anchor 554, shuttle closure 546 and pawl 536. During use (e.g., when the applicator handle 500B is coupled to the applicator needle hub assembly of FIG. 15, and one or more implants are loaded into the lumen of the needle), wheel subassembly of the applicator handle can be scroll-wheel actuated to advance the pusher wire 534 and eject one or more implants from the lumen of the needle.

TABLE 3

Materials used in the ENV515 Phase 2b-3A Implant Applicator Handle (part number 10539-325-149 Handle Assembly)

| Part Number | Qty | Component | Material | Comments |
| --- | --- | --- | --- | --- |
| 10539-325-75 REVE HANDLE - RIGHT | 1 | Custom, injection molded | 348-012002 COLOR: SNO WHITE | Injection molding grade of ABS with medium impact and high gloss, offering a good balance of physical properties, intermediate abuse resistance, and rigidity; Designated as "medical-grade" and has met the requirements of the USP Class VI and ISO 10993, Part I "Biological Evaluation of Medical Devices" tests with human tissue contact time of 30 days or less |
| 10539-325-74 RevD HANDLE - LEFT | 1 | Custom, injection molded | 348-012002 COLOR: SNO WHITE | Injection molding grade of ABS with medium impact and high gloss, offering a good balance of physical properties, intermediate abuse resistance, and rigidity; Designated as "medical-grade" and has met the requirements of the USP Class VI and ISO 10993, Part I "Biological Evaluation of Medical Devices" tests with human tissue contact time of 30 days or less |
| REF 92394A111 THREAD INSERT | 2 | OTS purchased component | MATERIAL: 18-8 STAINLESS STEEL | Standard off - the - shelf 304 stainless steel fastener |
| REF 91585A915 DOG BONE ANCHOR | 1 | OTS purchased component | MATERIAL: 18-8 STAINLESS STEEL | Standard off - the - shelf 304 stainless steel dowel pin |
| REF 92196A077 SOCKET HEAD CAP SCREW | 2 | OTS purchased component | MATERIAL: 18-8 STAINLESS STEEL | Standard off - the - shelf 304 stainless steel fastener |
| 10539-325-77 REVD PAWL | 1 | Custom purchased component (stamped) | 300 Series Stainless Steel | Meets ASTM A666 |
| 10539-325-202 RevA Wheel Axle | 1 | Custom, machined | MATERIAL: 300 SERIES STAINLESS STEEL | Standard 304 stainless steel machined to size, cleaned, and packaged |
| 10539-325-76 REVE WHEEL HUB | 1 | Custom, machined | RADEL ® R5500 COLOR: BLACK (BK937) | Material meets the requirements of USP Class VI specifications |
| 10539-325-72 REVD WHEEL RIM | 2 | Custom, injection molded | SANTOPRENE TPE 281- 73MED COLOR: NATURAL | Material meets the requirements of USP Class VI specifications |
| 10539-325-89 REVE PRIMARY PUSHER WIRE | 1 | Custom purchased component | MATERIAL: 304 STAINLESS STEEL | Spring Temper per ASTMA313 |
| 10539-325-84 RevB SHUTTLE BASE | 1 | Custom, injection molded | 348-012002 COLOR: SNO WHITE | Injection molding grade of ABS with medium impact and high gloss, offering a good balance of physical properties, intermediate abuse resistance, and rigidity; Designated as "medical-grade" and has met the requirements of the USP Class VI and ISO 10993, Part I "Biological Evaluation of Medical Devices" tests with human tissue contact time of 30 days or less |

TABLE 3-continued

Materials used in the ENV515 Phase 2b-3A Implant Applicator
Handle (part number 10539-325-149 Handle Assembly)

| Part Number | Qty | Component | Material | Comments |
|---|---|---|---|---|
| 10539-325-85 RevB SHUTTLE CLOSURE | 1 | Custom, injection molded | 348-012002 COLOR: SNO WHITE | Injection molding grade of ABS with medium impact and high gloss, offering a good balance of physical properties, intermediate abuse resistance, and rigidity; Designated as "medical-grade" and has met the requirements of the USP Class VI and ISO 10993, Part I "Biological Evaluation of Medical Devices" tests with human tissue contact time of 30 days or less |
| 10539-325-80 REVB DOG BONE SPRING | 1 | Custom, liquid silicone rubber (LSR) molded | ELASTOSIL ® LR 3003/50 A | Food grade (FDA CFR 21 § 177.2600 "Rubber articles intended for repeated use") |
| REF 8800K41 KEVLAR THREAD | 1 | OTS purchased component | MATERIAL: KEVLAR | Meets MIL-T-87128 |
| 10539-325-134 REVA POUCH - HANDLE | 1 | OTS purchased component | MATERIAL: HEAT SEAL COATED DUPONT TYVEK & 48 GA PET/1.5 MIL PE (35791-E) | Standard medical device packaging material manufactured of a layer of 1073B Tyvek Uncoated bonded to PET 48 Gauge film. Not included in biocomp tests but in contact with components prior to test |
| REF UV ADHESIVE LOCTITE UV3926 OR EQUIVALENT | 1 | OTS purchased component | MATERIAL: LOCTITE 3926 | High viscosity, UV/Visible light curing acrylic adhesive suitable for applications that require fast cure, flexibility, high adhesion and autoclave resistance. It is ISO 10993 Biological Tested of use in the assembly of disposable medical devices |
| REF LOCTITE 406 OR EQUIVALENT | 1 | OTS purchased component | MATERIAL: LOCTITE 406 | Wicking grade viscosity, surface insensitive instant adhesive designed for bonding of plastics and elastomeric materials where very fast fixturing is required |

ENV515 Gen 3 Implant Applicator Parts Directly in Contact with Human Subjects or ENV515 (travoprost) Intracameral Implants The ENV515 Gen 3 Implant Applicator parts that are in direct contact with the implant and with the human subject during the implant insertion into the anterior chamber of the eye consist of the 27G XTW 9.5 Degree Primary Grind Angle Needle (10539-325-232 REVD 27G XTW 9.5 DEGREE PRIMARY GRIND ANGLE NEEDLE) and stainless steel Secondary Pusher Wire Extended (10539-325-233 REVA SECONDARY PUSHER WIRE EXTENDED) (FIG. 1 and Table 1). The ENV515 (travoprost) Intracameral Implant(s) are loaded into the ENV515 Phase Gen 3 Applicator immediately before use through the bevel of the needle. During the administration procedure, the injection is conducted via clear peripheral cornea, during which the needle and the applicator shaft is in contact with clear peripheral cornea for less than 20 sec. The 27G XTW 9.5 Degree Primary Grind Angle Needle is a custom manufactured, 27 gauge, single-lumen hypodermic needle, manufactured by established hypodermic needle manufacturer ISPG, Inc., as discussed above. After assembly of the needle to its hub, a visual inspection is performed to verify the edge quality of the needle bevel followed by extensive testing. The Secondary Pusher Wire Extended comprises a straightened wire of 304 stainless steel (FIG. 1 and Table 1).

Sequential steps of a process for the manufacturing of the ENV515 Gen 3 Implant Applicator, according to some embodiments, are shown in Table 4.

TABLE 4

Steps in the Manufacture of the ENV515 Gen 3 Implant Applicator

| Step of the Manufacturing Process | Manufacturer |
|---|---|
| 1. Component acquisition, injection molding or machining | EG-Gilero, Medacys, ISPG, Proto Labs, Inc., C-Axis, Inc, Wytech Industries, JMC Tool and Machine Co., Atlantic Precision Spring, Inc., Biolink Lifesciences Inc. |
| 2. Wash needles and place into transport carriers | Oberg Industrial Machine & Tool, Inc. |
| 3. Functional test of needle sharpness | EG-GILERO |
| 4. Inspection and release of all components including dimensions and other attributes captured in Component Quality Plan and Certificate of Conformance | EG-GILERO |
| 5. Assembly of implant applicator | EG-GILERO |
| 6. Functional test of all implant applicators | EG-GILERO |
| 7. Packaging of implant applicators | EG-GILERO |
| 8. Labeling of packaged implant applicators | EG-GILERO |

TABLE 4-continued

Steps in the Manufacture of the ENV515 Gen 3 Implant Applicator

| Step of the Manufacturing Process | Manufacturer |
| --- | --- |
| 9. Gamma irradiation batch sterilization | STERIS Isomedix Services |
| 10. Finished goods QA | EG-GILERO |

In summary, in some embodiments, components can be acquired, injection molded, and/or machined. In some embodiments, a needle can be precision manufactured by an established hypodermic needle manufacturer following the methods and/or designs disclosed herein. In some embodiments, some or all components undergo inspection and are released prior to assembly. Patient contact components of the needle hub assembly undergo thorough washing with deionized water, ethanol, and/or the like. Needles and pusher wires can additionally undergo depyrogenation, and the implant applicators can then be fully assembled.

According to some embodiments, each implant applicator needle hub assembly and handle is separately and individually packaged, for example, in a Tyvek™ pouch (Heat Seal Coated CR27 1073B DuPont Tyvek & 48GA PET/1.5 MIL PE (35791-E)—BEMIS), and shipped to the contract sterilizer with appropriate documentation to be sterilized via a validated sterilization procedure. The sterilized implant applicators can undergo the following tests: sterilization validation and sterility testing, package integrity (seal peel and bubble emission emersion tests), biocompatibility (cytotoxicity, hemolysis, sensitization, acute systemic toxicity, and irritation), endotoxin, particulate matter, limits of acidity and alkalinity and limits for extractable metals, dimensional measurements, and functional evaluation (loading and ejection of ENV515 implants and needle penetration measurements), as described herein. Additional testing is conducted under accelerated aging conditions and under warehouse conditions as described herein (see "Stability Summary and Conclusions [ENV515 Phase Gen 3 Implant Applicator]").

Labeling of the ENV515 Gen 3 Implant Applicator

The labels applied to the Tyvek pouch are designed by Envisia Therapeutics and will, at a minimum, contain the following information:
Lot number
Expiration date
Manufacturer information
Available by prescription only
Sterile
Single use
Damage warnings
Non-pyrogenic A representative example of the label is provided below. The ENV515 Gen 3 Implant Applicator can be used for the purposes of the ENV515-01 Phase 2a Cohort 3 clinical study and provided to study sites as a Clinical Trial Material Kit containing ENV515 (travoprost) Intracameral Implants and the ENV515 Gen 3 Implant Applicator. Example labels for the kit, implants, and implant applicator are provided below.

ENV515 Kit Label

Sponsor: Envisia Therapeutics Inc. Durham, NC 27703 Ph: (919)973-1440

Protocol Number: ENV515-01

KIT ID: XXXXXX

ENV515-3-2 (travoprost) Intracameral Implant: 26.1 µg travoprost/implant

Contents: (5) ENV515-3-2 sterile implants, (3) plastic sterile field drapes, (2) sterile ocular drapes Dose to be loaded into applicator: 2 implants Opening instructions:

1. Use sterile technique in sterile field to open primary packaging for the applicator (provided separately) and ENV515 implants.

2. Open ENV515 Implant Applicator packaging and place the sterile ENV515 applicator into sterile field.

3. Do not open glass vial containing implants until ready to load into the applicator.

Instructions for loading the implant into the applicator by the Trained Investigator or Trained Envisia staff member:

1. Load ENV515 implants into the ENV515 Implant Applicator in a sterile field using sterile technique via insertion through the beveled needle end.

Key Instructions for administration by Trained Investigator:

1. Instill 2nd dose of VIGAMOX ® into the study eye (1st dose is administered during ocular exams).

2. Treat patient's ocular surface with topical anesthetic (proparacaine 0.5% or equivalent).

3. Treat patient's ocular surface with povidone iodine and wait 2 minutes.

4. Insert lid speculum.

5. Administer the implants into the anterior chamber via intracameral injection through clear, peripheral cornea.

The needle should be advanced parallel with the iris, ~1 mm anterior to the limbus with the patient sitting at the slit lamp, or with the patient supine under the operating scope.

-continued

6. Instill 3rd dose of VIGAMOX into the study eye.
Storage: Store at 2 to 8° C., excursions permitted to 15° C. (59° F.).
Return instructions: Please refer to Investigational Medicinal Product Manual for return instruction.
Caution: New Drug. Limited by Federal (or United States) law to Investigational Use.
Caution: To be used by Trained Investigator only.

Adhesive label legend:
1 = Kit ID. (Sponsor filled)
2 = Protocol Number: ENV515-01
4 = Lot No. 1616-038
5 = Subject ID. (Investigator filled)
6 = Investigator (Investigator filled)
7 = Date Administered (Investigator filled)

ENV515 (travoprost) Intracameral Implant Sterile Vial Label

ENV515-3-2 (travoprost) Intracameral Implant - 26.1 1ag Travoprost (knock out area)
Sponsor: Envisia Therapeutics Inc. (Durham, NC)
Caution: Administer per protocol instructions.
For intracameral route of administration only.
Caution: New Drug. Limited by Federal (or United States) law to Investigational Use.
Storage: Store at 2 to 8° C. with excursions up to 15° C. (59° F.)
LOT/DOM ENV515 Gen 3 Implant Applicator Label ENV515 Gen 3 Implant Applicator
Lot No.: XXXXXX
Sponsor: Envisia Therapeutics Inc. (Durham, NC)
Dose to be loaded into applicator: 2 implants
Caution: Handle only in sterile field - see ENV515 (travoprost) Intracameral Implant Kit Label for details.
Caution: Investigational device. Limited by Federal (or United States) law to investigational use.
Caution: To be used by Trained Investigator only.
See Kit Label for details.
Storage: Store at up to 25° C., excursions permitted to 30° C. (86° F.)
Sterile. Non-pyrogenic.

Manufacturers

A list of manufacturers, including subcontractors, is provided in Table 5.

TABLE 5

| Drug Product Manufacturers | |
|---|---|
| Name and Address | Responsibility |
| EG-GILERO<br>4022 Stirrup Creek Drive, Suite 300<br>Research Triangle Park, NC 27703 | Device design; maintenance of design history files; accelerated aging |
| EG-GILERO<br>6966 US220<br>Asheboro, NC 27205 | Device manufacturing |
| Medacys<br>C6, Min Zhuo Industrial Park<br>Guang Ming New District<br>Shenzhen, Guangdong Province, China | Component manufacturing |

TABLE 5-continued

| Drug Product Manufacturers | |
|---|---|
| Name and Address | Responsibility |
| ISPG, Inc.<br>10504 Technology Terrace<br>Lakewood Ranch, FL 34211 | Component manufacturing |
| Wytech Industries<br>960 E Hazelwood Ave.<br>Rahway, NC 07065 | Component manufacturing |
| Oberg Industrial Machine and Tool, Inc.<br>108 East Wilson Ave.<br>Norfolk, NE 68702 | Component manufacturing |
| C-Axis Inc.<br>MN 800 Tower Drive<br>Hamel, MN 55340 | Component manufacturing |
| Protolabs Inc.<br>5540 Pioneer Creek Dr.<br>Maple Plain, MN 55359 | Component manufacturing |
| JMC Machine and Tool Co.<br>5910 Elwin Buchanan Dr.<br>Sanford, NC 27330 | Component manufacturing |
| Atlantic Precision Spring, Inc.<br>125 Ronzo Rd<br>Bristol, CT 06010 | Component manufacturing |
| BioLink Life Sciences, Inc.<br>250 Quade Drive<br>Cary, NC 17513 | Component manufacturing |
| STERIS Isomedix Services<br>Radiation Technology Center<br>2500 Commerce Drive<br>Libertyville, IL 60048 | Gamma sterilization of assembled ENV515 Phase 2b-3A Implant Applicators |
| Wuxi AppTec<br>1265 Kennestone Cir.<br>Marietta, GA 30066 | Final release testing: biocompatibility, endotoxin, cytotoxicity; particulate |
| Pace Analytical Life Sciences<br>1311 Helmo Ave North<br>Oakdale, MN 55128 | Final release testing: limits of acidity and alkalinity and limits of extractable metals |
| DDL, Inc<br>10200 Valley View Road #101<br>Eden Prairie, MN 55344 | Final release testing: environmental conditioning; shipping and handling |

Container Closure

Following assembly and inspection, the ENV515 Gen 3 Implant Applicator was packaged in a Tyvek™ pouch (Heat Seal Coated CR27 1073B Dupont Tyvek & 48GA PET/1.5 MIL PE (35791-E)—BEMIS for both Needle Hub and Handle Assemblies) and terminally sterilized via gamma irradiation in accordance with a validated sterilization method. The integrity of the pouch was tested after complete assembly, packaging, sterilization, environmental conditioning/simulated shipping and after accelerated aging. Additionally, further testing is ongoing according to schedule described herein under "Stability Summary and Conclusions [ENV515 Gen 3 Implant Applicator]."

The ENV515 Phase Gen 3 Implant Applicator is supplied in two separate sterile packages: one containing the ENV515 Gen 3 Implant Applicator needle hub assembly (part number 10539-325-211 RevF ENV515 Generation 3 Implant Applicator—Needle Hub Assembly) and one containing the ENV515 Phase 2b-3A Implant Applicator handle (part number 10539-325-149 Handle Assembly).

Following assembly, the ENV515 Gen 3 Implant Applicator was packaged in a Tyvek™ pouch (Heat Seal Coated CR27 1073B Dupont Tyvek & 48GA PET/1.5 MIL PE (35791-E)—BEMIS) and terminally sterilized via gamma irradiation in accordance with a validated sterilization method. The integrity of the pouch was tested after shipping followed by conditioning and after accelerated aging at elevated temperature as described in the verification testing sections.

Verification Testing

The ENV515 Phase Gen 3 Implant Applicator, composed of the ENV515 Gen 3 Implant Applicator needle hub assembly (part number 10539-325-211 RevF ENV515 Gen 3 Implant Applicator—Needle Hub Assembly) and the ENV515 Phase 2b-3A Implant Applicator handle (part number 10539-325-149 Handle Assembly), underwent design verification testing to ensure design specifications were met in the manufactured devices. The ENV515 Phase 2b-3A Implant Applicator has been subjected to and passed release testing (or pilot design verification testing) after complete assembly, packaging, sterilization, environmental conditioning/simulated shipping and after accelerated aging as set forth herein.

The release testing after complete assembly, packaging, sterilization, environmental conditioning and simulated shipping consisted of the following tests: sterilization validation and sterility testing; package integrity (seal peel and bubble emission tests), biocompatibility (cytotoxicity, hemolysis, sensitization, acute systemic toxicity, and irritation), endotoxin, particulate matter, limits of acidity and alkalinity and limits for extractable metals, dimensional measurements, and functional evaluation (loading and ejection of ENV515 implants and needle penetration measurements). The testing after accelerated aging simulating 9 month shelf life consisted of package integrity testing (seal peel and bubble emission tests) and functional evaluation (loading and ejection of ENV515 implants and needle penetration measurements)

Implant Applicator Batches

A designated batch of ENV515 Phase Gen 3 Implant Applicators needle hub assemblies was manufactured for use in the ENV515-01 Phase 2a Cohort 3 clinical study: Needle Hub Assembly part number 10539-325-211 RevF ENV515 Generation 3 Implant Applicator—Needle Hub Assembly, lot number 3976. A designated batch of ENV515 Phase 2b-3A Implant Applicators handles was manufactured for use in the ENV515-01 Phase 2a Cohort 2 and 3 clinical study: Handle Assembly part number 10539-325-149/Rev F, lot number 2594.

All tests were conducted with these single batches of ENV515 Phase Gen 3 Implant Applicator needle hub assemblies and the ENV515 Phase 2b-3A Implant Applicators handles. The data provided in the "Control of Drug Product [ENV515 Gen 3 Implant Applicator]" and in "Stability Summary and Conclusions [ENV515 Gen 3 Implant Applicator]" sections herein were generated with ENV515 Phase Gen 3 Implant Applicators needle hub assemblies manufactured in the single clinical batch intended for ENV515-01 Phase 2a Cohort 3 clinical study and with the with ENV515 Phase 2b-3a Implant Applicators handles manufactured in the single clinical batch intended for ENV515-01 Phase 2a Cohort 2 and 3 clinical studies.

Design Verification—Introduction

EG-GILERO is supporting the development of the ENV515 Generation 3 Needle Hub Assembly (NHA) and Handle Assembly for Envisia Therapeutics. The sections that follow summarize the activities and responsibilities confirming, with objective evidence, that devices are acceptable for clinical evaluation after accelerated aging to an equivalent age of 9 months. The ENV515 Generation 3 Needle Hub Assembly (NHA) and Handle Assembly are sterile devices which are packaged separately and joined just prior to clinical use.

Scope

The data summarized below include the results for the following testing, in accordance with protocol 10539-440-08P revA ENV515 Gen 3 Pilot Design Verification Protocol—T=8 month (note that the protocol calls out a minimum of 8 months accelerated aging. During execution of the protocol, samples were accelerated aged for 9 months, meeting this minimum conditioning requirement of the test):
Needle Hub Assembly (P/N 10539-325-211, lot 3976): accelerated age testing (T=9 month)

Objective

The purpose of the following data objectively establishes that the Envisia Therapeutics ENV515 Generation 3 NHA at time T=9 months meets product requirements. In order to evacuate NHA samples, Handle Assembly samples need to be attached during testing. The Handle Assembly samples connected to the NHA samples during the execution of the protocol were re-used following real time testing (refer to 10539-440-07R for Handle Assembly results). The materials tested herein are for clinical use only, under IND controls through Envisia Therapeutics.

REFERENCES

ISO 7864:2016 Sterile Hypo Needles for Single Use, Devices tested to third edition
ISO 9626:2016 Stainless steel needle tubing for the manufacture of medical devices
ASTM-F1886-16 Standard Test Method for Determining integrity of Seals for Flexible Packaging by Visual Inspection
ASTM F88/F88M-15 Standard Test Method for Seal Strength of Flexible Barrier Materials
ASTM F2096-11 Standard Test Method for Detecting Gross Leaks in Packaging by Internal Pressurization (Bubble Test)
ISO 11137-1:2006(E) Sterilization of health care products—Radiation—Requirements for development
10539-340-03 RevD Envisia Applicator Simulated Use Test Method
10001-340-02 RevB Seal Strength of Flexible Barrier Materials Test Method
10001-340-03 RevA Visual Inspection for Determining Integrity of Seals for Flexible Packaging Materials Test Method (ASTM F1886)
10001-340-04 RevA Leak Detection by Internal Pressurization—Bubble Test (ASTM F2096-11)

10001-340-05 Rev01 Needle Penetration Test Method
10001-340-06 RevA ISO 7864 Hypodermic Needle Test Method Each of the above references is herein expressly incorporated by reference in its entirety for all purposes.

Manufacturing

The components making up the ENV515 Generation 3 Needle Hub are summarized in the device bill of materials on the drawings (P/N 10539-325-211 RevF). Packaging is specified in 10539-325-126 RevA (NHA pouch) and 10539-325-131 RevA (shipper). Material information is documented an individual drawings for custom components. Information on the Handle Assembly samples utilized during testing is provided in document 10539-440-07R.

Production or production equivalent components and materials were used to manufacture the devices used for the testing reported herein. The following manufacturing lots were tested:

TABLE 6

Device Lot Information

| Part Number | Revision Level | Drawing Name | Description | Manufacturing Lot Number | Comments |
| --- | --- | --- | --- | --- | --- |
| 10539-325-211 | F | ENV515 Generation 3 Implant Applicator - Needle Hub Assembly | ENV515 Generation 3 Needle Hub Assembly | 3976 | N/A |
| 10539-325-149 | F | ENV515-3A Applicator - Pkg | ENV515 Handle Assembly | 2594 | Previously tested per 10539-440-07P and reported under10539-440-07R |

NHA assemblies used for T=9 month testing were max dose sterilized with gamma radiation (40 kGy-48 kGy).

Pre-Conditioning

Needle Hub Assemblies used for testing were subject to accelerated aging for 49 days at 50° C. for a shelf life equivalent of 9 months. Devices were aged in EG-GILE-RO's Environmental Chamber, monitored using A0181 Temperature Data Logger.

The NHA packaging was then tested for package integrity per ASTM F1886, ASTM F88, and ASTM F2096. The results of package integrity testing are provided under separate report (refer to 10539-345-10R Gen 3 NHA Package Integrity Report T=9 months).

Simulated Use Test Results

Simulated use testing was conducted. Data collected using the texture analyzer falls under a new calibration cycle of the test equipment, which was completed before testing was resumed.

Loading and Ejection of Implant, Visual Indication of Ejection

New implants (Envisia hatch Number 16066-4) provided by Envisia Therapeutics (approximately 210 μm×250 μm×1500 μm) were loaded into each of 39 Needle Hub Assemblies to verify that the implants fit in the needle and could be successfully ejected from the NHA using the Handle to activate the pusher wire. The devices tested for implant loading and ejection were prepared and loaded in the same manner that will be used in clinical studies. Two new implants were loaded into each test sample with tweezers under magnification. Implants were not reused. Implant depth was evaluated by assessing if the implants were visible past the heel of the needle. The Needle Hub Assembly sample was capped end uncapped and then implants were ejected from the device. Ejection was verified by confirming the visibility of the pusher wire at the end of the needle.

All sample devices that were tested for loading and ejection of implants and visual indication of ejection passed. Results are summarized in Table 8.

TABLE 8

Results of loading and ejecting two implants in each devise

| Sample Number | Sample ID | Do the implants easily slide into the needle? | With 2 implants loaded, are all of the implants past the heel? | Are both implants ejected from the device | Is the secondary pusher visible at the end of the cannula? |
| --- | --- | --- | --- | --- | --- |
| 1 | 3976-T9-01 | Yes | Yes | Yes | Yes |
| 2 | 3976-T9-02 | Yes | Yes | Yes | Yes |
| 3 | 3976-T9-03 | Yes | Yes | Yes | Yes |
| 4 | 3976-T9-04 | Yes | Yes | Yes | Yes |
| 5 | 3976-T9-05 | Yes | Yes | Yes | Yes |
| 6 | 3976-T9-06 | Yes | Yes | Yes | Yes |
| 7 | 3976-T9-07 | Yes | Yes | Yes | Yes |
| 8 | 3976-T9-08 | Yes | Yes | Yes | Yes |
| 9 | 3976-T9-09 | Yes | Yes | Yes | Yes |
| 10 | 3976-T9-11 | Yes | Yes | Yes | Yes |
| 11 | 3976-T9-12 | Yes | Yes | Yes | Yes |
| 12 | 3976-T9-13 | Yes | Yes | Yes | Yes |

TABLE 8-continued

Results of loading and ejecting two implants in each devise

| Sample Number | Sample ID | Do the implants easily slide into the needle? | With 2 implants loaded, are all of the implants past the heel? | Are both implants ejected from the device | Is the secondary pusher visible at the end of the cannula? |
|---|---|---|---|---|---|
| 13 | 3976-T9-14 | Yes | Yes | Yes | Yes |
| 14 | 3976-T9-15 | Yes | Yes | Yes | Yes |
| 15 | 3976-T9-16 | Yes | Yes | Yes | Yes |
| 16 | 3976-T9-17 | Yes | Yes | Yes | Yes |
| 17 | 3976-19-18 | Yes | Yes | Yes | Yes |
| 18 | 3976-T9-21 | Yes | Yes | Yes | Yes |
| 19 | 3976-T9-23 | Yes | Yes | Yes | Yes |
| 20 | 3976-T9-25 | Yes | Yes | Yes | Yes |
| 21 | 3976-T9-26 | Yes | Yes | Yes | Yes |
| 22 | 3976-T9-27 | Yes | Yes | Yes | Yes |
| 23 | 3976-T9-29 | Yes | Yes | Yes | Yes |
| 24 | 3976-T9-30 | Yes | Yes | Yes | Yes |
| 25 | 3978-T9-31 | Yes | Yes | Yes | Yes |
| 26 | 3976-T9-32 | Yes | Yes | Yes | Yes |
| 27 | 3976-T9-33 | Yes | Yes | Yes | Yes |
| 28 | 3976-T9-35 | Yes | Yes | Yes | Yes |
| 29 | 3976-T9-36 | Yes | Yes | Yes | Yes |
| 30 | 3976-T9-37 | Yes | Yes | Yes | Yes |
| 31 | 3976-T9-39 | Yes | Yes | Yes | Yes |
| 32 | 3976-T9-40 | Yes | Yes | Yes | Yes |
| 33 | 3976-T9-41 | Yes | Yes | Yes | Yes |
| 34 | 3976-T9-42 | Yes | Yes | Yes | Yes |
| 35 | 3976-T9-43 | Yes | Yes | Yes | Yes |
| 36 | 3976-T9-44 | Yes | Yes | Yes | Yes |
| 37 | 3976-T9-45 | Yes | Yes | Yes | Yes |
| 38 | 3976-T9-46 | Yes | Yes | Yes | Yes |
| 39 | 3976-T9-47 | Yes | Yes | Yes | Yes |

Needle Length

The needle length from the end of the hub to the tip of the needle was measured using a vision measurement system. Acceptance criteria are 15 mm+0.3 mm.

TABLE 9

Equipment used for Needle Length

| Equipment |
|---|
| Micro-Vu (A0010) |

TABLE 10

Needle Length Data

| Sample ID | Record length of needle (mm) |
|---|---|
| 3976-T9-01 | 14.903 |
| 3976-T9-02 | 15.007 |
| 3976-T9-03 | 14.995 |
| 3976-T9-04 | 15.073 |
| 3976-T9-05 | 14.927 |
| 3976-T9-06 | 15.011 |
| 3976-T9-07 | 14.961 |
| 3976-T9-08 | 14.981 |
| 3976-T9-09 | 14.997 |
| 3976-T9-10 | 15.017 |
| 3976-T9-11 | 14.937 |
| 3976-T9-12 | 14.861 |
| 3976-T9-13 | 14.945 |
| 3976-T9-14 | 14.953 |
| 3976-T9-15 | 15.017 |
| 3976-T9-16 | 14.885 |
| 3976-T9-17 | 14.995 |
| 3976-T9-18 | 14.887 |
| 3976-T9-19 | 14.977 |

TABLE 10-continued

Needle Length Data

| Sample ID | Record length of needle (mm) |
|---|---|
| 3976-T9-21 | 14.919 |
| 3976-79-22 | 14.955 |
| 3976-T9-23 | 14.883 |
| 3976-T9-24 | 15.017 |
| 3976-T9-25 | 15.019 |
| 3975-T9-26 | 14.967 |
| 3976-T9-27 | 15.007 |
| 3976-T9-28 | 14.973 |
| 3976-T9-29 | 14.935 |
| 3976-T9-30 | 15.035 |
| 3978-T9-60 | 14.963 |

Needle length was collected as variable data. The data was examined for normality and then analyzed to ensure the 95% confidence limits for moderate severity. For these acceptance criteria, the K value used was 2.140 (for a two-sided interval). The results were analyzed using Minitab and determined to be normal.

Figure 17:
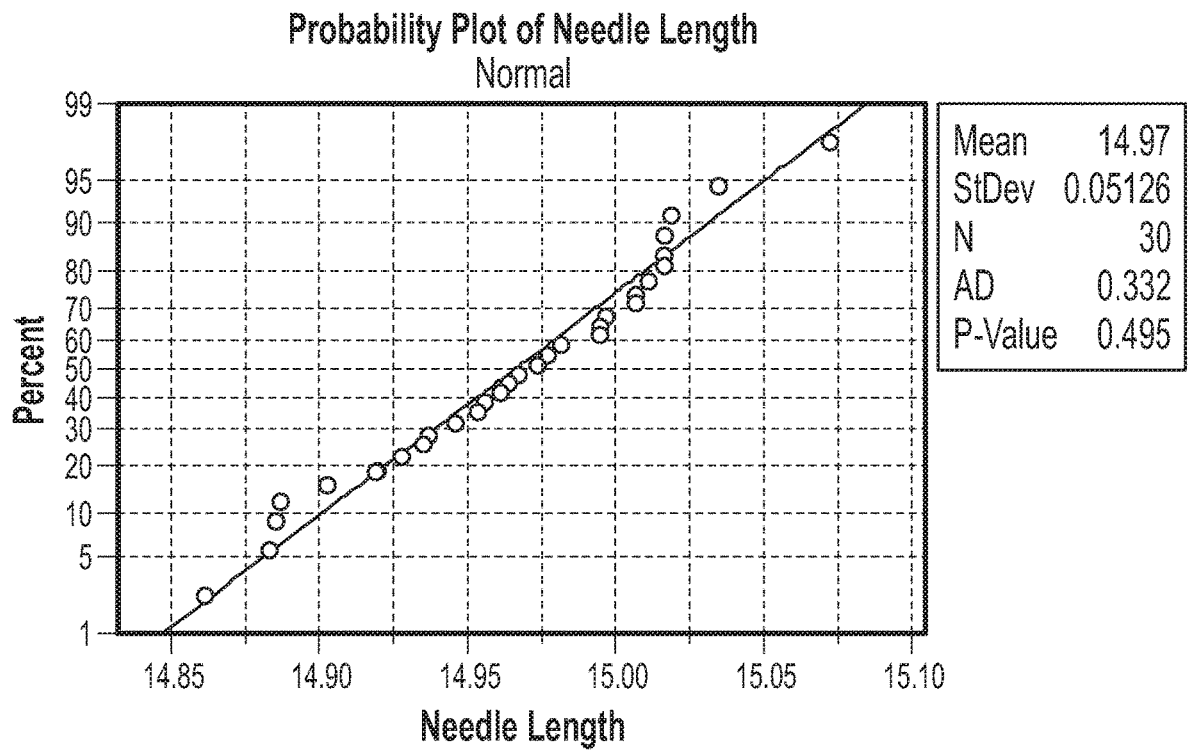
FIG. 17 is a probability plot of needle length, according to some embodiments.

FIG. 17 is a probability plot of needle length, according to some embodiments. LCL/UCL calculations are provided in Table 11 below.

TABLE 11

LCL and UCL Calculated Results

| LSL | 14.7 mm | LCL | 14.9 mm |
|---|---|---|---|
| USL | 15.3 mm | UCL | 15.1 mm |

To be acceptable, UCL<USL and LCL>LSL. The data for needle length complies and is acceptable variable data for moderate severity.

Devices Free of Debris

Visual inspection of debris is conducted with normal or corrected to normal vision. The devices were inspected immediately after removal from the sterile packaging. Any visible debris was considered a failure.

TABLE 12

Debris Inspection Results

| Sample ID | Is the Needle Hub Assembly free of debris? |
|---|---|
| 3976-T9-01 | Yes |
| 3976-T9-02 | Yes |
| 3976-T9-03 | Yes |
| 3976-T9-04 | Yes |
| 3976-T9-05 | Yes |
| 3976-T9-06 | Yes |
| 3976-T9-07 | Yes |
| 3976-T9-08 | Yes |
| 3976-T9-09 | Yes |
| 3976-T9-10 | Yes |
| 3976-T9-11 | Yes |
| 3976-T9-12 | Yes |
| 3978-T9-13 | Yes |
| 3976-T9-14 | Yes |
| 3976-T9-15 | Yes |
| 3976-T9-16 | Yes |
| 3976-T9-17 | Yes |
| 3976-T9-18 | Yes |
| 3976-T9-19 | Yes |
| 3976-T9-21 | Yes |
| 3976-T9-22 | Yes |
| 3976-T9-23 | Yes |
| 3976-T9-24 | Yes |
| 3976-T9-25 | Yes |
| 3976-T9-26 | Yes |
| 3976-T9-27 | Yes |
| 3976-T9-28 | Yes |
| 3976-T9-29 | Yes |
| 3976-T9-30 | Yes |
| 3976-T9-31 | Yes |
| 3976-T9-32 | Yes |
| 3976-T9-33 | Yes |
| 3976-T9-34 | Yes |
| 3976-T9-35 | Yes |
| 3976-T9-36 | Yes |
| 3976-T9-37 | Yes |
| 3976-T9-38 | Yes |
| 3976-T9-39 | Yes |
| 3976-T9-40 | Yes |
| 3976-T9-41 | Yes |
| 3976-T9-42 | Yes |
| 3976-T9-43 | Yes |
| 3976-T9-44 | Yes |
| 3976-T9-45 | Yes |
| 3976-T9-46 | Yes |
| 3976-T9-47 | Yes |
| 3976-T9-48 | Yes |
| 3976-T9-49 | Yes |
| 3976-T9-50 | Yes |
| 3976-T9-51 | Yes |
| 3976-T9-52 | Yes |
| 3976-T9-53 | Yes |
| 3976-T9-54 | Yes |
| 3976-T9-55 | Yes |
| 3976-T9-56 | Yes |
| 3976-T9-57 | Yes |
| 3976-T9-58 | Yes |
| 3976-T9-59 | Yes |
| 3976-T9-60 | Yes |

Needle Penetration Force

Needle penetration was measured with a penetration speed of 100 mm/min. The needle hub assembly was leaded do the crosshairs of the force analyzer and lowered slowly to penetrate a 0.4 mm polyurethane film. Measurements were taken for informational purposes and are provided in Table 14.

TABLE 13

Equipment used for Needle Penetration

| Equipment |
|---|
| Texture Analyzer (A0031) |
| Texture Analyzer (A0031) |
| 5 kg Load Cell (A0035) |
| 5 kg Load Cell (A0035) |

TABLE 14

Needle Penetration Force Results

| Sample ID | Force at F1 (Newtons) |
|---|---|
| 3976-T9-01 | 0.4281 |
| 3976-79-02 | 0.3690 |
| 3976-T9-03 | 0.4164 |
| 3976-T9-04 | 0.4596 |
| 3976-T9-05 | 0.3756 |
| 3976-T9-06 | 0.3855 |
| 3976-T9-07 | 0.3716 |
| 3976-T9-08 | 0.3810 |
| 3976-T9-09 | 0.4176 |
| 3976-T9-11 | 0.3671 |
| 3976-T9-12 | 0.4297 |
| 3976-T9-13 | 0.3633 |
| 3976-T9-14 | 0.3693 |
| 3976-T9-15 | 0.3812 |
| 3976-T9-16 | 0.4251 |
| 3976-T9-17 | 0.3914 |
| 3976-T9-18 | 0.4327 |
| 3976-T9-21 | 0.4450 |
| 397E-T9-23 | 0.4126 |
| 3976-T9-25 | 0.4087 |
| 3976-T9-25 | 0.3777 |
| 3976-T9-27 | 0.3979 |
| 3976-T9-29 | 0.4413 |
| 3976-T9-30 | 0.3926 |
| 3976-T9-31 | 0.4725 |
| 3976-T9-32 | 0.4960 |
| 3976-T9-33 | 0.4411 |
| 3976-T9-35 | 0.4274 |
| 3976-T9-36 | 0.4252 |
| 3976-T9-37 | 0.4251 |

The requirement for needle penetration force is to be determined as the product is under clinical development. 0.667 N was used for the upper specification limit for this statistical analysis for informational purposes only.

Needle penetration was collected as variable data. As stated in the protocol, the data was examined for normality and then analyzed to ensure the 95% confidence limits for severe criteria. Because needle penetration is a one-sided specification, a K value of 2.220 was used for the one-sided interval. The results were analyzed using Minitab and determined to be normal.

Figure 18:
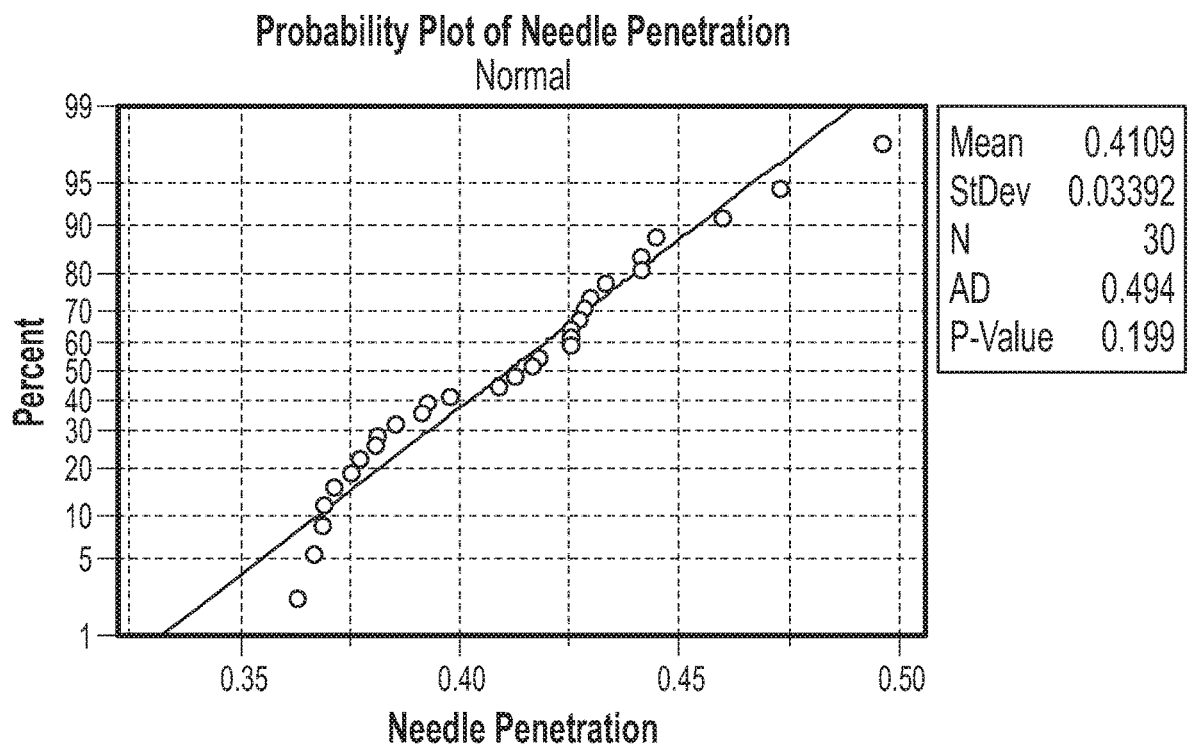
FIG. 18 is a probability plot of needle penetration, according to some embodiments.

FIG. 18 is a probability plot of needle penetration, according to some embodiments. The UCL calculation is provided in Table 15 below.

TABLE 15

UCL Calculated Results

| USL | 0.667N | UCL | 0.486N |
|---|---|---|---|

To be acceptable, UCL<USL. The data for needle penetration complies and is acceptable variable data for severe criteria.

Lubricant and Needle Point Visual Inspection

The needle of the NHA was inspected per ISO 7864 Section 11.4 (Lubricant) and Section 12 (Needle Point). The lubricant inspection requires that no lubricant be visible as droplets of fluid on the surfaces of the needle. The Needle Point inspection requires that the needle appear sharp and free from feather edges, burrs, and hooks under 2.5× magnification (Olympus SZ61 Microscope).

TABLE 16

Needle Point Inspection Results

| Sample ID | Does the needle meet the Lubricant Requirement? | Does the needle meet the Needle Point Requirement? |
|---|---|---|
| 3976-T9-01 | Yes | Yes |
| 3976-T9-02 | Yes | Yes |
| 3976-T9-03 | Yes | Yes |
| 3976-T9-04 | Yes | Yes |
| 3978-T9-05 | Yes | Yes |
| 3976-T9-06 | Yes | Yes |
| 3976-T9-07 | Yes | Yes |
| 3976-T9-08 | Yes | Yes |
| 3976-T9-09 | Yes | Yes |
| 3976-T9-10 | Yes | Yes |
| 3976-T9-11 | Yes | Yes |
| 3976-T9-12 | Yes | Yes |
| 3976-T9-13 | Yes | Yes |
| 3976-T9-14 | Yes | Yes |
| 3976-T9-15 | Yes | Yes |
| 3976-T9-16 | Yes | Yes |
| 3976-T8-17 | Yes | Yes |
| 3976-T9-18 | Yes | Yes |
| 3976-T9-19 | Yes | Yes |
| 3976-T9-21 | Yes | Yes |
| 3976-T9-22 | Yes | Yes |
| 3876-T9-23 | Yes | Yes |
| 3976-T9-24 | Yes | Yes |
| 3976-T9-25 | Yes | Yes |
| 3976-T9-26 | Yes | Yes |
| 3976-T9-27 | Yes | Yes |
| 3976-T9-28 | Yes | Yes |
| 3976-T9-29 | Yes | Yes |
| 3976-T9-30 | Yes | Yes |
| 3976-T9-31 | Yes | Yes |
| 3976-T9-32 | Yes | Yes |
| 3976-T9-33 | Yes | Yes |
| 3976-T9-34 | Yes | Yes |
| 3976-T9-35 | Yes | Yes |
| 3976-T9-36 | Yes | Yes |
| 3976-T9-37 | Yes | Yes |
| 3976-T9-38 | Yes | Yes |
| 3976-T9-39 | Yes | Yes |
| 3976-79-40 | Yes | Yes |
| 3976-T9-41 | Yes | Yes |
| 3976-79-42 | Yes | Yes |
| 3976-T9-43 | Yes | Yes |
| 3976-T9-44 | Yes | Yes |
| 3976-T9-45 | Yes | Yes |
| 3976-T9-46 | Yes | Yes |
| 3976-T9-47 | Yes | Yes |
| 3976-T9-48 | Yes | Yes |
| 3976-T9-49 | Yes | Yes |
| 3976-T9-50 | Yes | Yes |
| 3976-T9-51 | Yes | Yes |
| 3976-T9-52 | Yes | Yes |
| 3976-T9-53 | Yes | Yes |
| 3976-T9-54 | Yes | Yes |
| 3976-T9-55 | Yes | Yes |
| 3976-T9-56 | Yes | Yes |
| 3976-T9-57 | Yes | Yes |
| 3976-T9-58 | Yes | Yes |
| 3976-T9-59 | Yes | Yes |
| 3976-T9-60 | Yes | Yes |

CONCLUSION

In the completed pilot design verification testing, The ENV515 2B-3A Generation 3 Applicator met the criteria that allowed its clinical use in glaucoma patients.

Control of Drug Product [ENV515 Gen 3 Implant Applicator]

Envisia Therapeutics follows design control regulations in accordance with 21 CFR Part 820. A complete design history file has been established and maintained, covering design and development planning, design input, design output, design review, pilot design verification, design transfer and history of design changes. The ENV515 Gen 3 Implant Applicator consists of a newly designed and manufactured ENV515 Gen 3 Needle Hub Assembly (part number 10539-325-211 RevF ENV515 Gen 3 Implant Applicator—Needle Hub Assembly) paired with a previously manufactured and tested ENV515 Phase 2b-3A Implant Applicator Handle (part number 10539-325-149 Handle Assembly).

The ENV515 Gen 3 Needle Hub Assemblies have been subjected to and have passed release testing (or lot performance verification testing) after complete assembly, packaging, sterilization, environmental conditioning/simulated shipping and after accelerated aging.

ENV515 Phase 2b-3A Implant Applicator Handles were previously subjected to and have passed release testing (or lot performance verification testing) after complete assembly, packaging, sterilization, environmental conditioning/simulated shipping and after accelerated aging as set forth herein.

The release testing after complete assembly, packaging, sterilization, environmental conditioning and simulated shipping consisted of the following tests: sterilization validation and sterility testing; package integrity (seal peel and bubble emission emersion tests), biocompatibility (cytotoxicity, hemolysis, sensitization, acute systemic toxicity, and irritation), endotoxin, particulate matter, limits of acidity and alkalinity and limits for extractable metals, dimensional measurements, and functional evaluation (loading and ejection of ENV515 implants and needle penetration measurements). The testing after accelerated aging consisted of package integrity testing (visual inspection, seal peel and bubble emission emersion tests) and functional evaluation (loading and ejection of ENV515 implants and needle penetration measurements).

The applicator is supplied in two separate sterile packages: one containing the ENV515 Gen 3 Needle Hub Assembly (part number 10539-325-211 Needle Hub Assembly) and one containing the ENV515 Phase 2b-3A Implant Applicator Handle (part number 10539-325-149 Handle Assembly).

A designated batch of ENV515 Gen 3 Needle Hub Assemblies was manufactured for use in the ENV515-02

Phase 2b Cohort 3 clinical study: Needle Hub Assembly part number 10539-325-211, Revision F, lot number 3976.

A designated batch of ENV515 Phase 2b-3A Applicator Handles were manufactured for use in the ENV515-01 Phase 2a Cohort 2 clinical study: Handle Assembly part number 10539-325-149, Revision F, lot number 2594. Handle assemblies from this lot will also be used in the ENV515-02 Phase 2b Cohort 3 clinical study.

All tests and data below were generated with ENV515 Gen 3 Needle Hub Assemblies manufactured in the clinical batch intended for the ENV515-01 Phase 2a Cohort 3 clinical study. Following the completion of the release testing described below, a Certificate of Conformance was issued to certify that the ENV515 Gen 3 Needle Hub Assembly release testing passed all design verification tests (Test CoC).

Sterilization Validation and Analysis

The ANSI/AAMI/ISO 13004:2013 VDmax 25 guideline was used to perform a validation of the sterilization of the ENV515 Gen 3 Needle Hub Assembly via gamma radiation. The sterilization analysis included three components: bioburden determination, sublethal dose verification, and sterility testing.

Bioburden Determination

Ten non-irradiated samples from the clinical batch of the ENV515 Gen 3 Needle Hub Assemblies were randomly selected for bioburden testing and sent to Biotest Laboratories. Aerobic, fungal, spore, and obligate anaerobic burden counts were performed on each applicator sample, and bioburden recovery efficiency was determined using product inoculation. The average adjusted bioburden was <5.2 CFUs per needle hub assembly. A verification dose (SAL 10-1) was selected based upon the average bioburden results and referencing Table 9 in ANSI/AAMI/ISO 13137-2:2013. The closest number equal to or greater than the average bioburden was used. The verification dose was 6.5 kGy±10% for the needle hub assembly.

Sublethal Dose Verification

Following the establishment of the verification dose, thirteen samples of needle hub assemblies (10 samples for sterility testing and 3 for bacteriostasis/fungistasis) from the clinical batch of the ENV515 Gen 3 Needle Hub Assemblies were prepared for testing and sent to STERIS. The irradiation of test units was conducted with a delivered dose range of 6.20 to 6.25 kGy for sterility samples and with a delivered dose range of 42.30 to 44.15 KGy for bacteriostasis/fungistasis samples. These samples were then processed and shipped to Biotest Laboratories for testing.

Sterility and Bacteriostasis/Fungistasis Testing

Sterility testing on the clinical batch of ENV515 Gen 3 Needle Hub Assemblies was conducted by Biotest Laboratories in an ISO Class 5 hood in an ISO Class 6 cleanroom. A GMP sterility test of 10 ENV515 Gen 3 Needle Hub Assemblies was performed using the immersion method in soybean casein digest broth with an incubation period of 14 days at 30° C.; none of the tested samples exhibited growth in this test. Bacteriostasis/fungistasis testing was performed on 3 samples from Sublethal Dose Verification. ENV515 Gen 3 Needle Hub Assemblies were not found to be bacteriostatic or fungistatic. The results of these two tests substantiate a minimum dose of 25 kGy for a Sterility Assurance Level of 10-6 for the clinical batch of ENV515 Gen 3 Needle Hub Assemblies.

Sterilization Via Gamma Irradiation of the ENV515 Gen 3 Clinical Batch

Sterilization via gamma irradiation of the ENV515 Gen 3 Needle Hub Assemblies was conducted at the production dose of 27.5 to 40.0 kGy. The actual delivered dose was measured as 31.0 to 33.7 kGy (Sterilization Certificate).

Sterilization Validation Summary

Gamma irradiation sterilization was validated as an acceptable means of sterilization for the ENV515 Gen 3 Implant Applicator Needle Hub Assembly by STERIS [Report 16-069TT (ENV515 Gen 3 Needle Hub) and Sterilization Certificate]. The ANSI/AAMI/ISO11137-2:2013 (VDmax 25) guideline was followed to achieve a Sterility Assurance Level of 10-6.

The ANSI/AAMI/ISO 13004:2013 VDmax 25 guideline was also used to perform a validation of the sterilization of the ENV515 Phase 2b-3A Implant Applicator Handles via gamma radiation.

Gamma irradiation sterilization was validated (e.g., via sterilization analysis, including bioburden determination, sublethal dose verification, and/or sterility testing) as an acceptable means of sterilization for the ENV515 Phase 2b-3A Implant Applicator Handle by STERIS.

Environmental Conditioning and Simulated Shipping

Environmental conditioning on ENV515 Gen 3 Needle Hub Assemblies was performed per ISTA P2A (Test CoC). Simulated shipping (distribution simulation) was performed per ASTM D4169-14, DC 13, Assurance Level I (Test CoC).

Environmental conditioning and simulated shipping was previously performed on ENV515 Phase 2a-3B Implant Applicator Handles as described herein.

ENV515 Gen 3 Implant Applicator Testing after Complete Assembly, Packaging, Sterilization and Environmental Conditioning/Simulated Shipping Package Integrity Testing Package integrity testing was performed via visual inspection test, seal peel test and bubble emission emersion test on packaged ENV515 Gen 3 Needle Hub Assemblies, compliant with ASTM F1886, ASTM F88, and ASTM F2096. Forty (40) samples were designated for testing. Ten (10) samples were used for visual inspection and peel strength, while the remaining 30 samples were used for bubble emission emersion testing. All tested samples passed the visual test, peel strength and bubble emission emersion tests.

Package integrity testing was previously performed on packaged ENV515 Phase 2b-3A Implant Applicator Handles via visual inspection, seal peel, and bubble emission emersion tests, and all tested ENV515 Phase 2b-3A Implant Applicator Handle samples passed package integrity testing.

Biocompatibility Testing

In accordance with ISO 10993-1:2009, evaluation of the ENV515 Gen 3 Needle Hub Assembly was performed to ensure biocompatibility. The majority of the contact surface of the ENV515 Gen 3 Needle Hub Assembly is composed exclusively from the needle, which is a custom-designed and manufactured needle constructed from hypodermic medical grade 304 stainless steel conforming to ISO 9626:1991 for chemical compliance (see FIG. 1G—10539-325-232 Revision D 27G XTW 9.5 Degree Primary Grind Angle Needle).

Cytotoxicity, intracutaneous irritation and skin sensitization, acute systemic toxicity testing, and hemolysis were performed as conservative tests. This biocompatibility screening serves to confirm that the Envisia materials, manufacturing processes, and terminal sterilization via gamma irradiation cycle do not introduce unanticipated biocompatibility effects. These assessments were conducted per the ISO standards listed in Table 17.

Biocompatibility testing was conducted on ENV515 Gen 3 Needle Hub Assemblies by WuXi AppTec in accordance with Good Laboratory Practices (21 CFR 58). All testing met the defined acceptance criteria, as summarized in Table 17 below.

TABLE 17

ENV515 Gen 3 Needle Hub Assembly Biocompatibility Results

| Test | Acceptance Criteria | Results |
| --- | --- | --- |
| ISO 10993-5: 2009 Biological Evaluation of Medical Devices - Part 5: Tests for in vitro Cytotoxicity ISO L929 MEM Elution Test | Test Article < Grade 2 Mild Reactivity | Grade: 0 for needle hub assemblies Results: The test was considered valid as the control results were within acceptable parameters. The test articles received a score of Grade 0, indicating that the requirements of the ISO L929 MEM Elution Test have been met. |
| ISO 10993-10: 2010, Biological evaluation of medical devices - Part 10: Tests for Irritation and Skin Sensitization ISO Intracutaneous Reactivity Test | Test Article mean score - Control mean score <1.0 | Results: The test was considered valid based upon scientific judgment for the tested needle hub assembly samples. The differences in the mean test and control scores of the extract dermal observations were less than 1.0, indicating that the requirements of the ISO Intracutaneous Reactivity Test have been met by the test article. |
| ISO 10993-10: 2010, Biological evaluation of medical devices - Part 10: Tests for Irritation and Skin Sensitization ISO Guinea Pig Maximization Sensitization Test | Test Article < Grade 1 No erythema and edema | Results: None of the negative control animals challenged with the control vehicles were observed with a sensitization response greater than '0'. None of the animals challenged with the test article extracts from the needle hub assemblies were observed with a sensitization response greater than '0'. The normal saline extract of the test material had a sensitization response of '0' under valid test conditions. The sesame oil extract of the test material had a sensitization response of '0' under valid test conditions. Under the conditions of this protocol, the test article did not elicit a sensitization response. |
| ISO10993-11: 2010, Biological evaluation of medical devices - Part 11: Systemic Toxicity Testing ISO Acute Systemic Injection Test | None of the animals injected with test article extract may show a significantly greater biological reaction than the animals treated with control vehicle | Results: The control vehicle treated animals had no signs of toxicity at any of the observation periods and no animals lost weight in excess of 10%, indicating a valid test. None of the test needle hub assembly article extract treated animals were observed with clinical signs consistent with toxicity at any of the observation periods. Body weight changes were within acceptable parameters over the course of the study. These findings indicate that the requirements of the ISO Acute Systemic Injection Test have been met by the test article. |

TABLE 17-continued

ENV515 Gen 3 Needle Hub Assembly Biocompatibility Results

| Test | Acceptance Criteria | Results |
|---|---|---|
| ASTM method F756-13 Testing of hemolytic potential of the test article and its extract | None of the results based on the direct contact with test article or with its extract should demonstrate increased hemolytic potential over negative control | Results: Based on the criteria set forth in the protocol, the assay was valid. All of the tested needle hub assembly samples were considered nonhemolytic under the conditions employed. |

Cytotoxicity testing was previously performed on ENV515 Phase 2b-3A Implant Applicator, and all tested ENV515 Phase 2b-3A Implant Applicator Handle samples passed cytotoxicity test acceptance criteria listed in Table 17 above.

Pyrogenicity Testing

Pyrogenicity testing was performed in accordance with the USP <85> Bacterial Endotoxin Test, USP <161> "Transfusion and Infusion Assemblies and Similar Medical Devices", and FDA Guidance for Industry "Pyrogen and Endotoxin Testing: Questions and Answers" on a lot by lot basis as part of the ENV515 Gen 3 Needle Hub Assembly release process. The ENV515 Gen 3 Needle Hub Assembly conforms to test per the intended use of the ENV515 Gen 3 Implant Applicator (Report 1053088), with <0.05 EU/needle hub assembly.

Pyrogenicity testing in accordance with USP <85> Bacterial Endotoxin Test, USP <161> Transfusion and Infusion Assemblies and Similar Medical Devices, and FDA Guidance For Industry "Pyrogen and Endotoxin Testing: Questions and Answers" was previously performed on ENV515 Phase 2b-3A Implant Applicator Handles.

All tested ENV515 Phase 2b-3A Implant Applicator Handle samples conformed to test per their intended use.

Particulate Matter Testing

ENV515 Gen 3 Needle Hub Assemblies were tested for the content of particulate matter with the USP <788> Particulate Matter in Injections—Light Obscuration Method by WuXi AppTec (Test Code 400710.1, Report 42413). The results of the Environment and Resolution Tests indicated a valid assay. The tested number of particles within the extracted needle hub assembly samples remained low across particle size ranges of ≥10 µm, ≥25 µm and ≥50 µm (Test Code 400710.1, Report 42413).

Testing for Acidity, Alkalinity and Extractable Metals

ENV515 Gen 3 Needle Hub Assemblies were tested for acidity, alkalinity, and extractable metals under ISO 7864 (Annex A, Sections 5 and 6). The tested samples met specifications for being within one pH unit within the control (pH value of the control measured at 5.058; pH value of the tested sample 4.970 (Report 1762675). All tested samples were below level of quantification for individually tested extractable metals (Cd, Fe, Pb, Sn, Zn) and below level of quantification in a combined test for Pb, Zn, Sn and Fe (Report 1762675).

Dimensional Testing

ENV515 Gen 3 Needle Hub Assembly dimensional characteristics, including the needle length, were verified and found to conform (Test CoC).

Dimensional Testing for the ENV515 Phase 2b-3A Implant Applicator Handle was performed.

All dimensional characteristics of the ENV515 Phase 2b-3A Implant Applicator Handle were found to conform.

Custom Needle Testing

The ENV515 Gen 3 Needle Hub Assembly uses a custom manufactured 27 gauge, single-lumen hypodermic needle manufactured by commercial hypodermic needle manufacturer ISPG, and as such was tested to requirements described in ISO 7864:2016—Sterile Hypodermic Needles for Single Use. Requirements included testing for cleanliness, needle tube conformance, needle tube length tolerance, lubricant inspection, needle point inspection, freedom from defects, and patency of needle lumen. The ENV515 Gen 3 Needle Hub Assembly was found to conform to all ISO 7846:2016 requirements tested (Test COC).

Functional Testing

Envisia has conducted functional testing of the ENV515 Gen 3 Needle Hub Assembly composed of a needle insertion force test for a representative sample of ENV515 Gen 3 Needle Hub Assemblies from the clinical build batch, and a simulated use functional test for fully assembled and prepared ENV515 Gen 3 Implant Applicators. Simulated use functional testing was composed of loading two ENV515-3-2 implants into the ENV515 Gen 3 Implant Applicator and actuating the applicator to verify that the device ejects ENV515-3-2 implants as designed following actuation of the scroll wheel trigger. Implant applicators were prepared and loaded in the same manner that will be used during clinical dosing. The ENV515 Gen 3 Implant Applicator assembled device (consisting of ENV515 Gen 3 Needle Hub Assembly and ENV515 Phase 2b-3A Implant Applicator Handle) was found to conform (Test CoC).

Functional Testing for the ENV515 Phase 2b-3A Implant Applicator Handle was performed, and all functional testing results for the ENV515 Phase 2b-3A Implant Applicator Handle were found to confirm.

Further testing on the ENV515 Phase 2b-3A Implant Applicator Handle is ongoing.

ENV515 Gen 3 Implant Applicator Testing after Complete Assembly, Packaging, Sterilization and Accelerated Aging Following final assembly, packaging, and sterilization, the ENV515 Gen 3 Needle Hub Assemblies were exposed to accelerated aging at elevated temperature simulating 9 months of shelf-life. The testing after accelerated aging consisted of package integrity testing (visual inspection, seal peel and bubble emission emersion tests) (Report 10539-345-10R) and functional evaluation (loading and ejection of ENV515 implants and needle penetration measurements) (Report 10539-440-08R). All samples used for testing were subjected to accelerated aging for 49 days at 50° C. for a shelf life equivalent of 9 months.

Package Integrity Testing of ENV515 Gen 3 Implant Applicators Exposed to Accelerated Aging Package integrity testing on packaged and accelerated aged ENV515 Gen 3 Needle Hub Assemblies was performed via visual inspection test, seal peel test and bubble emission emersion test (Report 10539-345-10R), compliant with ASTM F1886, ASTM F88, and ASTM F2096. 40 needle hub assembly samples were designated for testing. 10 samples were used for visual inspection and peel strength, while the remaining 30 samples were used for bubble emission emersion testing. All tested needle hub assembly samples passed the visual test, peel strength and bubble emission emersion tests (Report 10539-345-10R).

Package integrity testing on the packaged ENV515 Phase 2b-3A Implant Applicator Handle after accelerated aging was performed, and all tested ENV515 Phase 2b-3A Implant Applicator Handles passed the visual test, peel strength, and bubble emission emersion tests.

Functional Testing of ENV515 Phase 2b-3A Implant Applicators Exposed to Accelerated Aging The functional testing for ENV515 Gen 3 Needle Hub Assembly following accelerated aging was composed of needle insertion force testing and simulated use functional testing (Report 10539-440-08R). Simulated use functional testing was composed of loading two ENV515-3-2 implants into the fully assembled and prepared ENV515 Gen 3 Implant Applicator (consisting of accelerated aged ENV515 Gen 3 Needle Hub Assembly and ENV515 Phase 2b-3A Implant Applicator Handle) and actuating the applicator to verify that the device ejects ENV515-3-2 implants as designed following actuation of the scroll wheel trigger (Report 10539-440-08R). Implant applicators were prepared and loaded in the same manner that will be used during clinical dosing. The ENV515 Gen 3 Needle Hub Assembly was found to conform (Report 10539-440-08R).

Functional Testing for the ENV515 Phase 2b-3A Implant Applicator Handle after accelerated aging was previously performed, and all results were found to conform.

Further ENV515 Gen 3 Implant Applicator Testing

Further functional testing is in progress under warehouse condition storage (see section titled "Stability Summary and Conclusions [ENV515 Gen 3 Implant Applicator])," including the following steps: storage at warehouse conditions, followed by package integrity and functional testing according to a predetermined schedule.

Stability Summary and Conclusion [ENV515 Gen 3 Implant Applicator]

The ENV515 Phase Gen 3 Implant Applicator shelf-life is solely for the purpose of package integrity and full device functionality following shipment and storage as there are no components of the device with a finite useful life. A stability coverage enveloping the dosing period during which the ENV515 Phase 2b-3a Implant Applicator is used is provided via accelerated aging studies and warehouse condition real time studies. To assess shelf-life, an accelerated aging study was conducted and supports 9 months of shelf life. Additionally, real-time aging under warehouse conditions storage is ongoing, with full coverage over the dosing period of the ENV515-01 Phase 2a Cohort 3 clinical study (ENV515-01 Phase 2a Study Protocol incorporating Amendment 05). Additionally, supporting stability study of the ENV515 Phase 2a Implant Applicator has reported data with maintained all passing results through 30 months.

Stability Testing

The ENV515 Phase Gen 3 Implant Applicator consists of the ENV515 Gen 3 Implant Applicator needle hub assembly (part number 10539-325-211 RevF ENV515 Generation 3 Implant Applicator—Needle Hub Assembly) and the ENV515 Phase 2b-3A Implant Applicator handle (part number 10539-325-149 Handle Assembly).

Shelf-life testing includes ENV515 Phase Gen 3 Implant Applicator storage under accelerated aging conditions and warehouse conditions. These shelf-life studies are conducted, under both conditions, on the final, fully assembled, packaged, and sterilized batch of the ENV515 Gen 3 Implant Applicators manufactured for the ENV515-01 Phase 2a Cohort 3 clinical study.

After shipping and aging at accelerated and warehouse conditions, the following tests are carried out using warehouse and accelerated aging conditions: pouch integrity via a bubble emission test, seal integrity via a seal peel test, and device functional evaluation. These stability tests challenge the design of the product and package over time to ensure the design output meets the design input as specified in the Design Record in accordance with ISO 11607-1:2006 Packaging for terminally sterilized medical devices—Part 1: Requirements for materials, sterile barrier systems and packaging systems. These tests are conducted, at the schedule shown in Table 18, on the final, fully assembled, packaged, and sterilized batch of the ENV515 Gen 3 Implant Applicators manufactured for the ENV515-01 Phase 2a Cohort 3 clinical study.

TABLE 18

Stability Study Conditions and Test Schedule

| Group ID | Aging Conditions | Temperature | Time |
|---|---|---|---|
| 1 | Time 0 - Real time[b] | Typical warehouse conditions (15-30° C.) | 0 months |
| 2 | 3 Months - Real time[a] | Typical warehouse conditions (15-30° C.) | 3 months |
| 3 | 6 Months - Real time[a] | Typical warehouse conditions (15-30° C.) | 6 months |
| 4 | 9 Months - Real time[a] | Typical warehouse conditions (15-30° C.) | 9 months |
| 5 | 12 Months - Real time[a] | Typical warehouse conditions (15-30° C.) | 12 months |
| 6 | 24 Months - Real time[a] | Typical warehouse conditions (15-30° C.) | 24 months |
| 7 | 9 Months - Accelerated[b] | 50° C. | 49 days |

[a]Study is ongoing
[b]Study is completed

Both the warehouse condition and accelerated aging studies were designed to provide enveloping stability coverage for the dosing period for the planned ENV515-01 Phase 2a clinical study. The first patient to be dosed with the ENV515

Gen 3 Implant Applicator in the ENV515-01 Phase 2a Cohort 3 clinical study is planned after the completion of the Time 0 real time warehouse condition and accelerated condition testing and prior to the 3-month real time testing. The last patient, last dose is expected prior to the 3-month sample evaluation for the warehouse condition study (Table 1, Group 2, 3-month time point). The time 0 real time testing and the accelerated aging study is completed (see "Control of Drug Product [ENV515 GEN 3 Implant Applicator]" section) and provides 9-month coverage starting prior to first patient dosed with the ENV515 Gen 3 Implant Applicator and extending beyond the planned last patient, last dose.

Since the ENV515 (travoprost) Intracameral Implants are not pre-loaded into the ENV515 Phase Gen 3 Implant Applicator, and are packaged separately, ENV515 (travoprost) Intracameral Implant evaluation, including stability, is conducted separately in an appropriate container closure system (see "Container Closure" section herein).

Figure 19A:
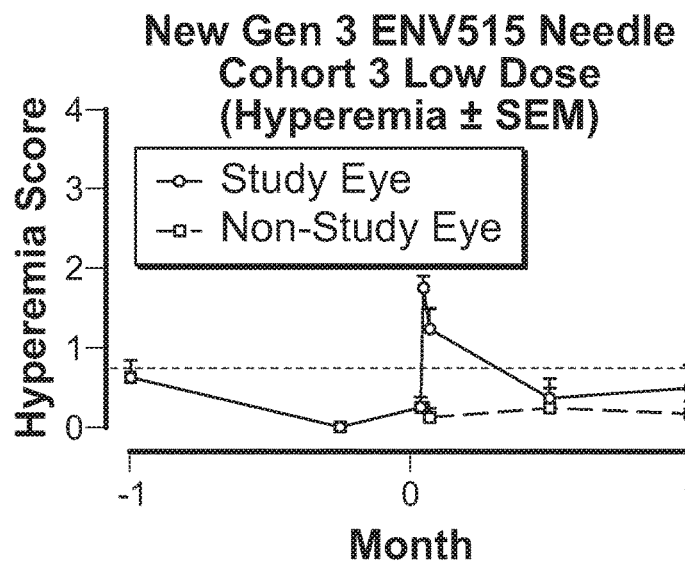
FIG. 19A is a plot of hyperemia score for the needle design of FIG. 1.
Figure 19B:
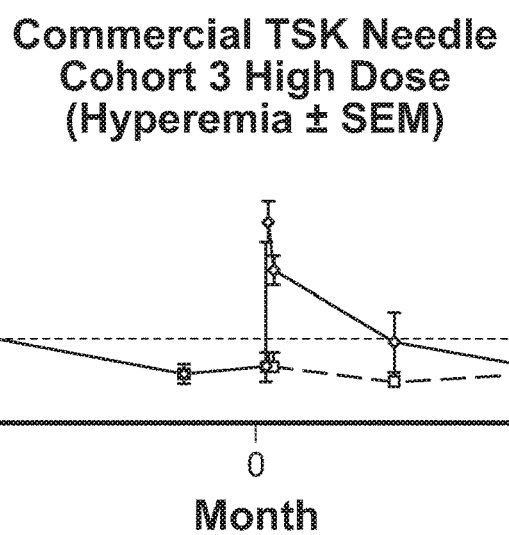
FIG. 19B is a plot of hyperemia score for a commercial needle manufactured by TSK Laboratory.
Figure 19C:
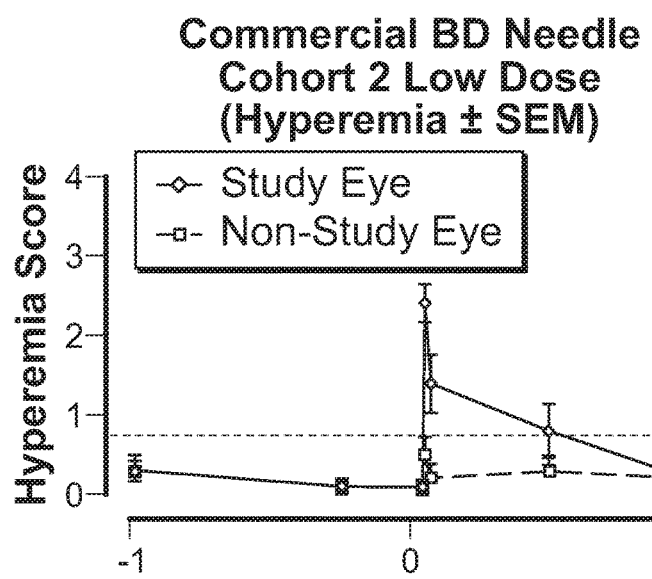
FIG. 19C is a plot of hyperemia score for a commercial needle manufactured by Becton Dickinson.

FIG. 19A is a time-based plot of hyperemia score for the needle Design A as shown in FIG. 1. Hyperemia, or ocular redness, was defined as using high resolution, color photograph scale that provided images of human eyes with no hyperemia and images representative of individual numerical scores, with higher number indicating greater extent and more severe hyperemia. For comparison purposes, FIG. 19B shows a plot of hyperemia score for a commercial needle manufactured by TSK Laboratory, and FIG. 19C shows a plot of hyperemia score a commercial needle manufactured by Becton Dickinson. In each of FIGS. 19A-19C, each plotted hyperemia score includes a superimposed error bar corresponding to standard error of the mean (SEM). As can be observed in referring to FIGS. 19A-19C, the hyperemia score has been consistently lower, as compared with historical controls, in all long term cohorts following intraocular injection with the Design A ENV515 needle. Hyperemia has also been consistently reduced as compared with historical topical PGA controls across all long term studies. As such, use of the improved injector needle Design A has been shown to result in a reduced severity and/or more rapid resolution (i.e., faster recovery) of hyperemia post-injection (Cohort 3 low dose).

Figure 20B:
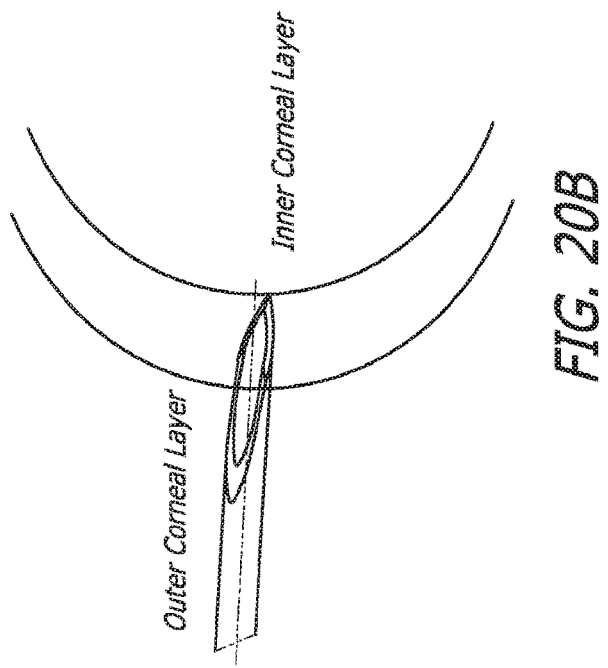
FIG. 20B illustrates the positioning of the needle transition during injection into an eye, according to some embodiments.
Figure 20A:
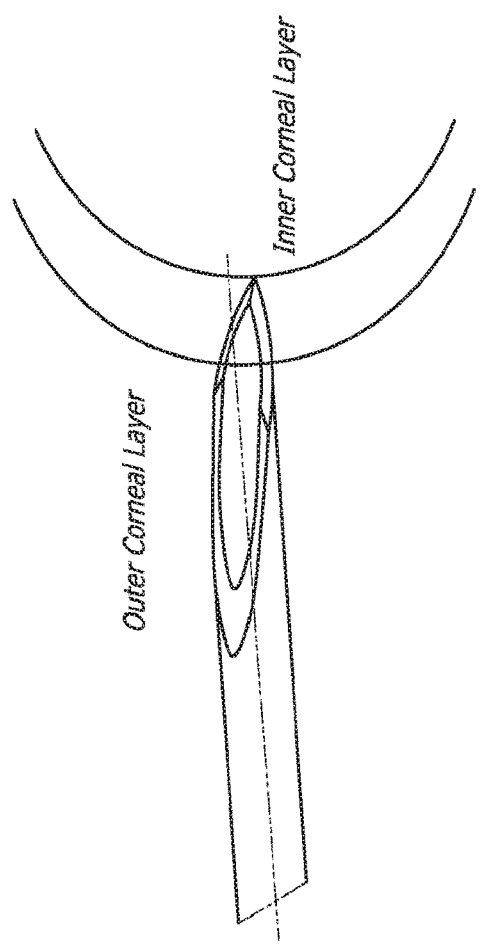
FIG. 20A illustrates the positioning of the needle transition during injection into an eye, according to some embodiments.

FIGS. 20A-20B illustrate the positioning of the needle transition during injection into an eye, according to some embodiments. In FIG. 20A, as the needle tip begins to penetrate the inner corneal layer, the transition is positioned outside the outer corneal layer and the inner corneal layer (i.e., the transition is not positioned between the outer corneal layer and the inner corneal layer, nor is it penetrating the outer corneal layer). Note that in FIG. 20B, as the needle tip begins to penetrate the inner corneal layer, the transition is positioned between the outer corneal layer and the inner corneal layer. As such, in each of the configurations shown in FIGS. 20A and 20B, the penetration of the needle transition through the outer corneal layer does not coincide with the needle tip's penetration of the inner corneal layer.

Although needle designs herein are described as being 27 gauge, other gauges of needle are also contemplated, and can benefit from the novel structural features set forth herein. Different bevel lengths may be needed for different needle gauges.

In some embodiments, it is beneficial for the transition between the primary and secondary bevels to occur outside of the cornea while the needle tip is penetrating the inner-most layer of cornea. In other embodiments, it is beneficial for the transition between the primary and secondary bevels to occur inside of the cornea while the needle tip is penetrating the inner-most layer of cornea, with the normal human corneal thickness being ~500-600 μm.

Additional Embodiments

In some embodiments, an apparatus comprises: a first cap; a second cap including a proximal end, a distal end, and a longitudinal axis; a needle hub connected to the second cap; a pusher wire and a pusher wire connector disposed within the needle hub; and an intracameral injector needle. The intracameral injector needle comprises: a substantially cylindrical body defining a longitudinal flow path therein, the body including a proximal end, a distal end, an outer peripheral face and a bevel region, the longitudinal flow path extending from the proximal end to the distal end, a first bevel of the bevel region having a first bevel angle with respect to the outer peripheral face; and a second bevel of the bevel region extending from the first bevel to the proximal end, the second bevel: (1) including a tip of the intracameral injector needle, and (2) having a second bevel angle with respect to the outer peripheral face, the second bevel angle different from the first bevel angle, the first bevel and the second bevel defining a transition therebetween, the bevel region having a tapered width. In some such embodiments, the transition is longitudinally positioned between the tip of the intracameral injector needle and a location of a maximum width of the bevel region. Alternatively or in addition, the transition can be vertically disposed at a position below 50% of a maximum height of the bevel region. The proximal end of the intracameral injector needle is configured to receive an implant, and the distal end of the intracameral injector needle is disposed within a hub pocket of the needle hub. The first cap is connected to the needle hub and disposed at a proximal end of the second cap, and the pusher wire, the pusher wire connector, and the intracameral injector needle are substantially aligned with one another along the longitudinal axis of the second cap. The pusher wire can be dimensioned such that it can be received in the bore of the intracameral injector needle. The pusher wire can be configured to engage, upon attachment to an applicator and during use, with an actuator of the applicator.

In some embodiments, an applicator comprises a wheel and is configured to receive an apparatus comprising: a first cap; a second cap including a proximal end, a distal end, and a longitudinal axis; a needle hub connected to the second cap; a pusher wire and a pusher wire connector disposed within the needle hub; and an intracameral injector needle. The intracameral injector needle comprises: a substantially cylindrical body defining a longitudinal flow path therein, the body including a proximal end, a distal end, an outer peripheral face and a bevel region, the longitudinal flow path extending from the proximal end to the distal end, a first bevel of the bevel region having a first bevel angle with respect to the outer peripheral face; and a second bevel of the bevel region extending from the first bevel to the proximal end, the second bevel: (1) including a tip of the intracameral injector needle, and (2) having a second bevel angle with respect to the outer peripheral face, the second bevel angle different from the first bevel angle, the first bevel and the second bevel defining a transition therebetween, the bevel region having a tapered width. In some such embodiments, the transition is longitudinally positioned between the tip of the intracameral injector needle and a location of a maximum width of the bevel region. Alternatively or in addition, the transition can be vertically disposed at a position below 50% of a maximum height of the bevel region. The proximal end of the intracameral injector needle is configured to receive an implant, and the distal end of the intracameral injector needle is disposed within a hub pocket of the needle hub. The first cap is connected to the needle hub and disposed at a proximal end of the second cap, and the pusher wire, the pusher wire connector, and the intracameral injector needle are substantially aligned with one another along the longitudinal axis of the second cap. The pusher wire can be dimensioned such that it can be received in the bore of the intracameral injector needle. The pusher wire can be configured to engage, upon attachment to an applicator and during use, with an actuator of the applicator. The applicator is configured to advance, during use, a single implant through the proximal end of the needle upon a predetermined partial rotation of the wheel.

In some embodiments, an apparatus comprises: a first cap; a second cap having a proximal end, a distal end, and a longitudinal axis, the second cap including a bristle retainer at least partially disposed therewithin at the distal end thereof, the bristle retainer having a bristle at least partially disposed therewithin; a needle hub at least partially disposed within the second cap; a needle including a proximal end and a distal end, the distal end disposed within a hub pocket of the needle hub; and at least one implant disposed within the needle, the first cap connected to the needle hub and disposed at a proximal end of the second cap, the needle and the at least one implant substantially aligned with one another along the longitudinal axis of the second cap. The needle is an intracameral injector needle comprising: a substantially cylindrical body defining a longitudinal flow path therein, the body including an outer peripheral face and a bevel region, the longitudinal flow path extending from the proximal end to the distal end, a first bevel of the bevel region having a first bevel angle with respect to the outer peripheral face; and a second bevel of the bevel region extending from the first bevel to the proximal end, the second bevel: (1) including a tip of the intracameral injector needle, and (2) having a second bevel angle with respect to the outer peripheral face, the second bevel angle different from the first bevel angle, the first bevel and the second bevel defining a transition therebetween, the bevel region having a tapered width. In some such embodiments, the transition is longitudinally positioned between the tip of the intracameral injector needle and a location of a maximum width of the bevel region. Alternatively or in addition, the transition can be vertically disposed at a position below 50% of a maximum height of the bevel region. The apparatus can further comprise a pusher wire disposed within the needle hub and configured to engage, upon attachment to an applicator and during use, with an actuator of the applicator. The bristle retainer can include a bristle retainer hub having one or more ribs on an exterior surface thereof, the one or more ribs configured to interference fit with the second cap. The needle hub can include one or more ribs on an exterior surface thereof, the one or more ribs configured for interference fit with the second cap. The needle and the needle hub are connected to one another (e.g., with an adhesive). The bristle can be partially fixed within the bristle retainer (e.g., with an adhesive).

In some embodiments, a method comprises: inserting an elongate portion of a load tool into a needle subassembly such that the elongate portion of the load tool substantially aligns with a longitudinal axis of the needle subassembly; inserting an implant in a first opening of the load tool; inserting an elongate portion of a pusher tool into the first opening of the load tool such that the implant is at least partially received within a bore of a needle of the needle subassembly; and removing the load tool from the needle subassembly. The elongate portion of the load tool is inserted into the needle subassembly at a proximal end of the needle subassembly, the method further comprising connecting a cap to the proximal end of the needle subassembly after removing the load tool from the needle subassembly.

In some embodiments, a delivery device comprises an elongated body member, wherein the elongated body member defines a long axis along its longest dimension, defines a top-plane for engaging a user, and when engaged by a user comprises a proximal end nearest the user and a distal end furthest from the user; and a cannula having an inner diameter and defining a long axis along the centerline of the cannula, wherein the long axis is oriented substantially parallel with the long axis of the elongated body member, and wherein the long axis of the cannula is not more than 7 millimeters below the top-plane of the elongated body member near the distal end of the elongated body member.

In some embodiments, an apparatus comprises: a cap having a proximal end, a distal end, and a longitudinal axis, the cap including a bristle retainer at least partially disposed therewithin at the distal end thereof, the bristle retainer having a bristle at least partially disposed therewithin; a needle hub at least partially disposed within the cap; a needle including a proximal end and a distal end, the proximal end including a bevel region and the distal end disposed within a hub pocket of the needle hub; an applicator connected to the needle hub; and at least one implant disposed within the needle, the needle and the at least one implant substantially aligned with one another along the longitudinal axis of the cap. The needle can be an intracameral injector needle comprising: a substantially cylindrical body defining a longitudinal flow path therein, the body including a proximal end, a distal end, an outer peripheral face and a bevel region, the longitudinal flow path extending from the proximal end to the distal end, a first bevel of the bevel region having a first bevel angle with respect to the outer peripheral face; and a second bevel of the bevel region extending from the first bevel to the proximal end, the second bevel: (1) including a tip of the intracameral injector needle, and (2) having a second bevel angle with respect to the outer peripheral face, the second bevel angle different from the first bevel angle, the first bevel and the second bevel defining a transition therebetween, the bevel region having a tapered width. In some such embodiments, the transition is longitudinally positioned between the tip of the intracameral injector needle and a location of a maximum width of the bevel region. Alternatively or in addition, the transition can be vertically disposed at a position below 50% of a maximum height of the bevel region.

In some embodiments, an apparatus comprises: a cap including a proximal end, a distal end, and a longitudinal axis; a preloaded needle hub assembly, the preloaded needle hub assembly including (a) a needle, and (b) a bristle disposed within a bristle retainer; wherein the needle hub assembly is connected to an applicator handle. The needle can be an intracameral injector needle comprising: a substantially cylindrical body defining a longitudinal flow path therein, the body including a proximal end, a distal end, an outer peripheral face and a bevel region, the longitudinal flow path extending from the proximal end to the distal end, a first bevel of the bevel region having a first bevel angle with respect to the outer peripheral face; and a second bevel of the bevel region extending from the first bevel to the proximal end, the second bevel: (1) including a tip of the intracameral injector needle, and (2) having a second bevel angle with respect to the outer peripheral face, the second bevel angle different from the first bevel angle, the first bevel and the second bevel defining a transition therebetween, the bevel region having a tapered width. In some such embodiments, the transition is longitudinally positioned between the tip of the intracameral injector needle and a location of a maximum width of the bevel region. Alternatively or in addition, the transition can be vertically disposed at a position below 50% of a maximum height of the bevel region. The apparatus can further comprise a pusher wire and a pusher wire connector disposed within the needle hub assembly and configured such that, in use, the pusher wire engages with one or more implants disposed within a bore of the needle. The applicator handle can be configured to actuate, and the pusher wire is configured such that, with each actuation of the applicator handle during use, a single implant disposed within the bore of the needle is linearly advanced.

Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

As used herein, the terms "about" and "approximately" generally mean plus or minus 10% of the value stated, e.g., about 250 μm would include 225 μm to 275 μm, about 1,000 μm would include 900 μm to 1,100 μm.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, the embodiments (e.g., of designing and/or utilizing disclosed needles) may be implemented using a variety of materials and methods. Further, it should be appreciated that the present needles and methods of making and operating needles may be used in conjunction with a computer, which may be embodied in any of a number of forms.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The use of flow diagrams is not meant to be limiting with respect to the order of operations performed. The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedia components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of," or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

All transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An ophthalmic injector needle comprising:
  a substantially cylindrical body defining a longitudinal flow path therein, the body including a first end, a second end, an outer peripheral face and a bevel region, the longitudinal flow path extending from the first end to the second end;
  a first bevel of the bevel region having a first bevel angle with respect to the outer peripheral face and a primary bevel rotation angle with respect to a midline of a needle cross-section; and
  a second bevel of the bevel region extending from the first bevel to the first end, the second bevel:
    (1) including a tip of the ophthalmic injector needle,
    (2) having a second bevel angle with respect to the outer peripheral face, the second bevel angle greater than the first bevel angle, and
    (3) having a secondary bevel rotation angle with respect to the midline of the needle cross-section, that is different from the primary bevel rotation angle;
  the first bevel and the second bevel defining a first transition and a second transition therebetween,
  the bevel region having a tapered width, and
  the first transition and the second transition longitudinally positioned between the tip of the ophthalmic injector needle and a location of a maximum width of the bevel region, and wherein a first length of the first bevel and a second length of the second bevel are configured based on a thickness of a biological membrane to prevent the first transition and the second transition from penetrating an outer layer of the biological membrane simultaneously as the tip penetrates an inner layer of the biological membrane when the ophthalmic injector needle is inserted through the biological membrane by having a ratio between the second length of the second bevel, as measured from the tip to the first transition and the second transition, and the first length of the first bevel, as measured from the first transition and the second transition to where the outer peripheral face and the bevel region meet, is between:
  1:0.97 and 1:4.93.

2. The ophthalmic injector needle of claim 1, wherein the first bevel angle with respect to the outer peripheral face is between about 7.5 degrees and about 11.5 degrees, the second bevel angle with respect to the outer peripheral face is between about 18 degrees and about 22 degrees, and the secondary bevel rotation angle with respect to the midline of the needle cross-section is between about 28 degrees and about 32 degrees.

3. The ophthalmic injector needle of claim 2, wherein the first bevel angle with respect to the outer peripheral face is about 9.5 degrees, the second bevel angle with respect to the outer peripheral face is about 20 degrees, and the secondary bevel rotation angle with respect to the midline of the needle cross-section is about 30 degrees.

4. The ophthalmic injector needle of claim 1, wherein the first bevel angle with respect to the outer peripheral face is between about 4 degrees and about 8 degrees, the second bevel angle with respect to the outer peripheral face is between about 11 degrees and about 15 degrees, and the secondary bevel rotation angle with respect to the midline of the needle cross-section is between about 33 degrees and about 37 degrees.

5. The ophthalmic injector needle of claim 1, wherein the first bevel angle with respect to the outer peripheral face is about 6 degrees, the second bevel angle with respect to the outer peripheral face is about 13 degrees, and the secondary bevel rotation angle with respect to the midline of the needle cross-section is about 35 degrees.

6. An intraocular injection device, comprising the ophthalmic injector needle of claim 1.

7. The intraocular injection device of claim 6, further comprising:
  a cap having a proximal end, a distal end, and a longitudinal axis, the cap including a bristle retainer at least partially disposed therewithin at the distal end thereof, the bristle retainer having a bristle at least partially disposed therewithin;
  a needle hub at least partially disposed within the cap;
  the ophthalmic injector needle disposed within a hub pocket of the needle hub;
  an applicator connected to the needle hub; and
  at least one implant disposed within the ophthalmic injector needle, the ophthalmic injector needle and the at least one implant substantially aligned with one another along the longitudinal axis of the cap.

8. A method of administering an implant to a patient, the method comprising:
  providing an ophthalmic injection device, including a preloaded needle hub assembly and an applicator handle, the preloaded needle hub assembly including: the ophthalmic injector needle of claim 1, an implant, and a bristle disposed within a bristle retainer;
  applying force to the ophthalmic injector needle to penetrate a biological membrane; and actuating the applicator handle such that the implant is linearly advanced through the ophthalmic injector needle.

9. The ophthalmic injector needle of claim 1, wherein a ratio between a first force used to penetrate the biological membrane from the tip to the first transition and the second transition compared to a second force used to penetrate the biological membrane from the first transition and the second transition to where the outer peripheral face and the bevel region meet is between:

1:1.05 and 1:1.66.

10. The ophthalmic injector needle of claim 1, wherein the biological membrane is an optical membrane and the first transition and the second transition are positioned less than 500 µm from the tip.

11. The ophthalmic injector needle of claim 1, wherein the first length and the second length are configured such that the first transition and the second transition are positioned within the biological membrane when the tip reaches the inner layer of the biological membrane.

12. The ophthalmic injector needle of claim 1, wherein the first length and the second length are configured such that the first transition and the second transition are positioned outside of the biological membrane when the tip reaches the inner layer of the biological membrane.

13. An ophthalmic injector needle comprising:
a first bevel of a bevel region having a first bevel angle with respect to an outer peripheral face; and
a second bevel of the bevel region extending from the first bevel, the second bevel:
(1) including a tip of the ophthalmic injector needle,
(2) having a second bevel angle with respect to the outer peripheral face, the second bevel angle different from the first bevel angle, and
(3) a secondary bevel rotation angle with respect to a midline of a needle cross-section,
the first bevel and the second bevel defining a first transition and a second transition therebetween,
the bevel region having a tapered height, and
the first transition and the second transition vertically disposed at a position below 50% of a maximum height of the bevel region, and wherein a first length of the first bevel and a second length of the second bevel are configured based on a thickness of a biological membrane to prevent the first transition and the second transition from penetrating an outer layer of the biological membrane simultaneously as the tip penetrates an inner layer of the biological membrane when the ophthalmic injector needle is inserted through the biological membrane,
wherein a ratio between the second length of the second bevel and the first length of the first bevel is between one of:
1:0.97 and 1:4.93;
1:1.24 and 1:3.09; and
1:0.66 and 1:1.84.

14. The ophthalmic injector needle of claim 13, wherein the first bevel angle with respect to the outer peripheral face is between about 7.5 degrees and about 11.5 degrees.

15. The ophthalmic injector needle of claim 14, wherein the first bevel angle with respect to the outer peripheral face is about 9.5 degrees.

16. The ophthalmic injector needle of claim 13, wherein the second bevel angle with respect to the outer peripheral face is between about 18 degrees and about 22 degrees.

17. The ophthalmic injector needle of claim 13, wherein the second bevel angle with respect to the outer peripheral face is about 20 degrees.

18. The ophthalmic injector needle of claim 13, wherein the ophthalmic needle is a 27 gauge needle.

19. An intraocular injection device, comprising the ophthalmic injector needle of claim 13.

20. The intraocular injection device of claim 19, further comprising:
a cap having a proximal end, a distal end, and a longitudinal axis, the cap including a bristle retainer at least partially disposed therewithin at the distal end thereof, the bristle retainer having a bristle at least partially disposed therewithin;
a needle hub at least partially disposed within the cap;
the ophthalmic injector needle disposed within a hub pocket of the needle hub;
an applicator connected to the needle hub; and
at least one implant disposed within the ophthalmic injector needle, the ophthalmic injector needle and the at least one implant substantially aligned with one another along the longitudinal axis of the cap.

21. A method of administering an implant to a patient, the method comprising:
providing an intraocular injection device, including a preloaded needle hub assembly and an applicator handle, the preloaded needle hub assembly including: the ophthalmic injector needle of claim 13, an implant, and a bristle disposed within a bristle retainer;
applying a first force to the ophthalmic injector needle to penetrate a biological membrane with the tip of the ophthalmic injector needle up to the first transition and the second transition;
applying, after penetrating the biological membrane up to the first transition and the second transition, a second force, to continue inserting of the ophthalmic injector needle past the first transition and the second transition;
wherein a ratio between a first force used to penetrate the biological membrane from the tip to the first transition and the second transition compared to a second force used to penetrate the biological membrane from the first transition and the second transition to where the outer peripheral face and the bevel region meet is between: 1:1.05 and 1:1.66; and
actuating the applicator handle such that the implant is linearly advanced through the ophthalmic injector needle.

* * * * *